(12) United States Patent
Jaeschke et al.

(10) Patent No.: US 7,947,685 B2
(45) Date of Patent: May 24, 2011

(54) PYRAZINE-2-CARBOXYAMIDE DERIVATIVES

(75) Inventors: Georg Jaeschke, Basel (CH); Sabine Kolczewski, Rheinfelden (DE); Richard Hugh Philip Porter, Reinach (CH); Eric Vieira, Frenkendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/470,554

(22) Filed: May 22, 2009

(65) Prior Publication Data

US 2009/0233944 A1 Sep. 17, 2009

Related U.S. Application Data

(63) Continuation of application No. 11/366,007, filed on Feb. 28, 2006, now abandoned.

(30) Foreign Application Priority Data

Mar. 4, 2005 (EP) .................................. 05101704

(51) Int. Cl.
*C07D 241/02* (2006.01)
*C07D 241/00* (2006.01)
*A61K 31/497* (2006.01)

(52) U.S. Cl. ..................... 514/252.1; 544/336; 544/408; 548/123; 548/146; 548/356.1

(58) Field of Classification Search ............. 514/255.05, 514/252.1, 359; 544/295, 405, 407, 242, 544/336, 408; 548/123, 356.1, 146
See application file for complete search history.

(56) References Cited

U.S. PATENT DOCUMENTS 7,414,060 B2 8/2008 Jaeschke et al.

FOREIGN PATENT DOCUMENTS

EP 0 321 115 6/1989
WO 2005/079802 9/2005

OTHER PUBLICATIONS

Taylor et al., "Pteridines . . . ", J'nal of American Chem. Society, 80(2), pp. 421-427, 1958.*
Felder et al., "Synthesis of 4(3H)-Pteridinones", J'nal of Med. Chem., 15(2), pp. 210-211, 1972.*
Bonnefous et al., Bioorganic & Medicinal Chemistry Letters, vol. 15, pp. 1197-1200 (2005).
Mutel, V., Expert Opinion Ther. Patents, vol. 12(12), pp. 1845-1852 (2002).
Schlaeger et al., Cytotechnology, vol. 30: pp. 71-83 (1999).
Ahn et al., J. Med. Chem. Vo. 40, pp. 2196-2210 (1997).
Felder et al., Jour. Of Med. Chem., 15(2), pp. 210-211 (1972).
Bonnefous et al., Bioorganic & Medicinal Chem. Letters, 15(4) pp. 1197-1200 (2004).
Taylor et al., J. of the American Chem. Society, vol. 80(2), pp. 421-427 (1958).
Felder et al., J. of Medicinal Chem. vol. 15(2), 1972, pp. 210-211.

* cited by examiner

*Primary Examiner* — Paul V. Ward
(74) *Attorney, Agent, or Firm* — George W. Johnston; Patricia S. Rocha-Tramaloni; Kimberly J. Prior

(57) ABSTRACT

The present invention is concerned with novel pyrazine 2-carboxyamide derivatives of formula (I)

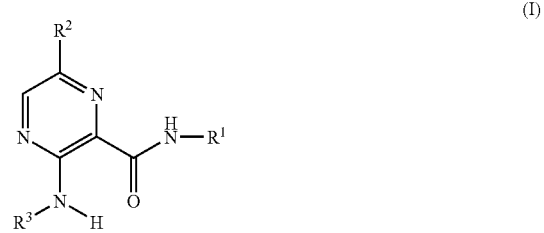

wherein $R^1$, $R^2$ and $R^3$ are as defined in the specification. These compounds are useful for the treatment of CNS disorders.

23 Claims, No Drawings

PYRAZINE-2-CARBOXYAMIDE DERIVATIVES

PRIORITY TO RELATED APPLICATIONS

This application is a continuation of U.S. application Ser. No. 11/366,007, filed Feb. 28, 2006, now pending; which claims the benefit of European Application No. 05101704.4, filed Mar. 4, 2005. The entire contents of the above-identified applications are hereby incorporated by reference.

BACKGROUND OF THE INVENTION

In the central nervous system (CNS) the transmission of stimuli takes place by the interaction of a neurotransmitter, which is sent out by a neuron, with a neuroreceptor. Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR families are known and of these some even have sub-types. According to their sequence homology, signal transduction mechanisms and agonist selectivity, these eight receptors can be sub-divided into three sub-groups: mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are gastroesophageal reflux disease (GERD), fragile X syndrome, ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, obesity, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

SUMMARY OF THE INVENTION

The present invention provides novel pyrazine 2-carboxyamide derivatives of formula (I)

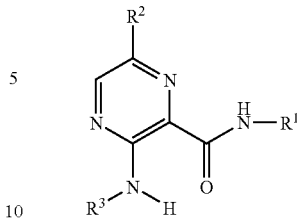

wherein
$R^1$ is a 5- or 6-membered ring of formula (II) or (III):

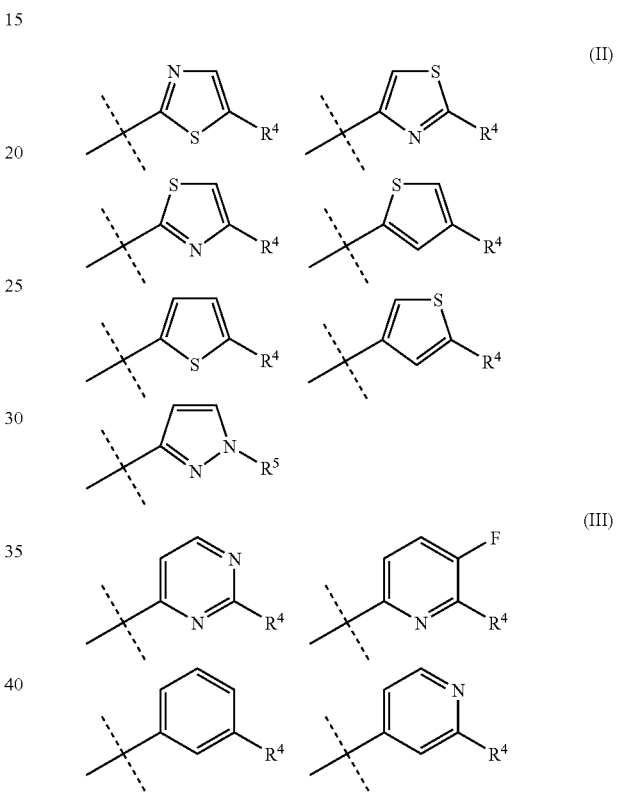

$R^2$ is H, $C_1$-$C_7$-alkyl, $C_3$-$C_6$-cycloalkyl, or —$(CH_2)_m$—$R^a$;
$R^3$ is H, aryl or heteroaryl each of which is optionally substituted by:
  CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —S(O)$_2$—$R^d$, or heteroaryl which is optionally substituted by $C_1$-$C_7$-alkyl;
$R^4$ is H, —OH, Cl, F, Br, CN, —$CHF_2$, $CF_3$, $C_1$-$C_7$-alkyl, —O—(CO)—$C_1$-$C_7$-alkyl, or —$(CH_2)_m$—$R^c$;
$R^5$ is $C_1$-$C_7$-alkyl, $C_1$-$C_7$-alkyl-$C_3$-$C_6$-cycloalkyl, —$(CH_2)_n$—O—$R^f$, $C_3$-$C_8$-alkenyl-O—$R^f$, —$(CH_2)_n$—$NR^gR^h$, —$C_2$-$C_6$-alkenyl-$NR^gR^h$, or —$(CH_2)_n$—$R^c$;
$R^a$ is —O—$C_1$-$C_7$-alkyl or —OH;
$R^b$ is $C_1$-$C_7$-alkyl, $NH_2$, or —O—$C_1$-$C_7$-alkyl;
$R^c$ is —OH, $NH_2$, or NH—(CO)—O—$C_1$-$C_7$-alkyl;
$R^d$ is $C_1$-$C_7$-alkyl, —$NH_2$, —NH—$C_1$-$C_7$-alkyl, or —N-di($C_1$-$C_7$-alkyl);
$R^e$ is —OH, —$CH_2F$, —$CHF_2$, —$CF_3$, or —O—(CO)—$C_1$-$C_7$-alkyl;
$R^f$ is $C_1$-$C_7$-alkyl, $C_3$-$C_8$-alkenyl, $C_3$-$C_6$-cycloalkyl, phenyl, benzyl, or —(CO)—R';

$R^g$ and $R^h$ are each independently H, $C_1$-$C_7$-alkyl, $C_3$-$C_6$-cycloalkyl, $C_3$-$C_8$-alkenyl, phenyl, benzyl, or —(CO)—R' or $R^g$ and $R^h$, together with the nitrogen atom to which they are attached, form a 5- to 7-membered heterocyclic or heteroaryl ring optionally substituted with 1 or 2 OH;

R' is $NH_2$, —NH—$C_1$-$C_7$-alkyl, $C_1$-$C_7$-alkyl, or $C_1$-$C_7$-alkoxy;

m is 1 to 4; and n is 2 to 6;

and pharmaceutically acceptable salts thereof.

Bonnefous et al. in Dipyridyl amides: potent metabotropic glutamate subtype 5 (mGlu5) receptor antagonists; *Bioorganic & Medicinal chemistry Letters,* 2005, described compounds useful as group I metabotropic glutamate receptor antagonists without disclosing the compounds of the instant invention. Furthermore, Bonnefous et al. disclosed that generally compounds of formula (I) where $R^1$ is pyridine-3-yl or pyridine-4-yl are inactive.

Contrary to this finding, the 5-position of said pyridine-2-yl compounds are indeed amenable to substitution by a fluorine atom, and the resulting compounds of formula I where $R^1$ is pyridine-4-yl are active as mGluR5 receptor antagonists. In addition, further pyrazine-2-carboxyamide derivatives other than pyridine-2-yl derivatives are active as mGluR5 receptor antagonists.

Compounds of general formula I are metabotropic glutamate receptor antagonists. Compounds of formula I are distinguished by having valuable therapeutic properties. They can be used for the treatment of mGluR5 receptor mediated disorders.

The present invention also provides pharmaceutical compositions containing compounds of the invention and methods for preparing the compounds and compositions of the invention. The invention further provides methods for treating mGluR5 receptor mediated disorders. For example, the invention provides methods for treating acute and/or chronic neurological disorders, in particular anxiety and chronic acute pain.

DETAILED DESCRIPTION OF THE INVENTION

The following definitions of general terms used in the present description apply irrespective of whether the terms in question appear alone or in combination. It must be noted that as used in the specification and the appended claims, the singular forms "a," "an," and "the" include plural forms unless the context clearly dictates otherwise.

"Aryl" means a monovalent cyclic aromatic hydrocarbon moiety consisting of a mono-, bi- or tricyclic aromatic ring. Preferred aryl groups are $C_6$-$C_{10}$ aryl. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"$C_1$-$C_7$ alkyl" denotes a straight- or branched-carbon chain group containing from 1 to 7 carbon atoms, for example, methyl, ethyl, propyl, isopropyl, isobutyl, sec-butyl, tert-butyl, pentyl, and n-hexyl as well as these specifically illustrated by the examples herein below.

"Alkenyl" denotes a straight- or branched-chain unsaturated hydrocarbon residue having 3-8, preferably 2-6, carbon atoms, such as ethenyl, 2-propenyl, and isobutene-1-yl, as well as those specifically illustrated by the examples herein below.

"Halogen" denotes chlorine, iodine, fluorine and bromine.

"Heteroaryl" means a monocyclic, bicyclic or tricyclic radical of 5 to 12, preferably 5 to 9, ring atoms having at least one aromatic ring and furthermore containing one, two, or three ring heteroatoms selected from N, O, or S, the remaining ring atoms being C. Heteroaryl can optionally be substituted with one, two, three or four substituents, wherein each substituent is independently hydroxy, cyano, alkyl, alkoxy, thioalkyl, halo, haloalkyl, hydroxyalkyl, alkoxycarbonyl, amino, acetyl, —NHCOOC($CH_3$)$_3$ or halogen substituted benzyl, or for the non aromatic part of cyclic ring also by oxo, unless otherwise specifically indicated. Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyrazinyl, optionally substituted pyridinyl, optionally substituted pyrimdinyl, optionally substituted indonyl, optionally substituted isoquinolinyl, optionally substituted carbazol-9-yl, optionally substituted furanyl, optionally substituted benzofuranyl, optionally substituted benzo[1,2,3]thiadiazolyl, optionally substituted benzo[b]thiophenyl, optionally substituted 9H-thioxanthenyl, optionally substituted thieno[2,3-c]pyridinyl and the like or these which are specifically exemplified herein.

"$C_3$-$C_6$ cycloalkyl" denotes a carbon ring having 3 to 6 carbon atoms as ring members and includes, but is not limited to, cyclopropyl, cyclobutyl, cyclopentyl, and cyclohexyl, as well as these groups specifically illustrated by the examples herein below.

"5- to 7-membered heterocyclic" denotes a saturated cyclic ring comprising from 1 to 6 carbon atoms as ring members, the other remaining ring member atoms being selected from one or more O, N, and S. Preferred 5 to 7 membered heterocycloalkyl groups are 5 or 6 membered heterocycloalkyl groups. Examples of 5 to 7 and 5 or 6 membered heterocycloalkyl groups include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiomorpholinyl, thiomorpholinylsulfoxide, thiomorpholinylsulfone, dihydroquinolinyl, dihydrisoquinolinyl, tetrahydroquinolinyl, tetrahydroisoquinolinyl, 1-oxo-thiomorpholin, 1,1-dioxo-thiomorpholin, 1,4-diazepane, and 1,4-oxazepane as well as these groups specifically illustrated by the examples herein below.

"Pharmaceutically acceptable," such as pharmaceutically acceptable carrier, excipient, etc., means pharmaceutically acceptable and substantially non-toxic to the subject to which the particular compound is administered.

The term "pharmaceutically acceptable salt" refers to any salt derived from an inorganic or organic acid or base.

"Therapeutically effective amount" means an amount that is effective to prevent, alleviate, or ameliorate symptoms of disease or prolong the survival of the subject being treated.

The present invention provides novel pyrazine 2-carboxyamide derivatives of formula (I)

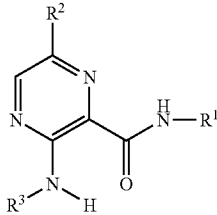

wherein
R¹ is a 5- or 6-membered ring of formula (II) or (III):

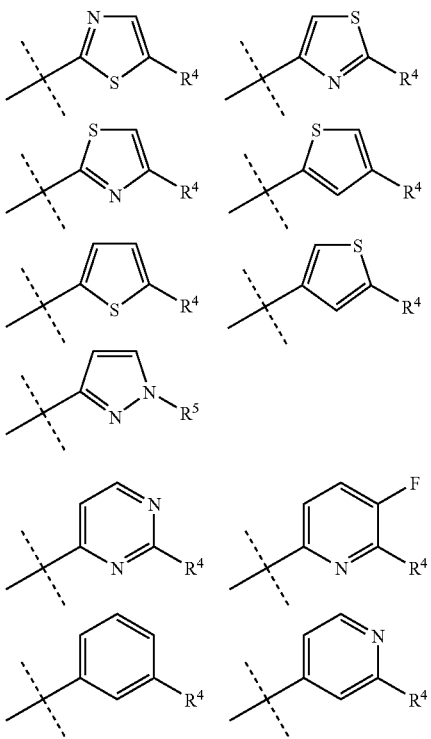

$R^2$ is H, $C_1$-$C_7$-alkyl, $C_3$-$C_6$-cycloalkyl, or —$(CH_2)_m$—$R^a$;
$R^3$ is H, aryl or heteroaryl each of which is optionally substituted by:
 CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —S(O)$_2$—$R^d$, or heteroaryl which is optionally substituted by $C_1$-$C_7$-alkyl;
$R^4$ is H, —OH, Cl, F, Br, CN, —$CHF_2$, $CF_3$, $C_1$-$C_7$-alkyl, —O—(CO)—$C_1$-$C_7$-alkyl, or —$(CH_2)_m$—$R^e$;
$R^5$ is $C_1$-$C_7$-alkyl, $C_1$-$C_7$-alkyl-$C_3$-$C_6$-cycloalkyl, —$(CH_2)_n$—O—$R^f$, $C_3$-$C_8$-alkenyl-O—$R^f$, —$(CH_2)_n$—$NR^gR^h$, —$C_2$-$C_6$-alkenyl-$NR^gR^h$, or —$(CH_2)_n$—$R^e$;
$R^a$ is —O—$C_1$-$C_7$-alkyl or —OH;
$R^b$ is $C_1$-$C_7$-alkyl, $NH_2$, or —O—$C_1$-$C_7$-alkyl;
$R^c$ is —OH, $NH_2$, or NH—(CO)—O—$C_1$-$C_7$-alkyl;
$R^d$ is $C_1$-$C_7$-alkyl, —$NH_2$, —NH—$C_1$-$C_7$-alkyl, or —N-di($C_1$-$C_7$-alkyl);
$R^e$ is —OH, —$CH_2F$, —$CHF_2$, —$CF_3$, or —O—(CO)—$C_1$-$C_7$-alkyl;

$R^f$ is $C_1$-$C_7$-alkyl, $C_3$-$C_8$-alkenyl, $C_3$-$C_6$-cycloalkyl, phenyl, benzyl, or —(CO)—R';
$R^g$ and $R^h$ are each independently H, $C_1$-$C_7$-alkyl, $C_3$-$C_6$-cycloalkyl, $C_3$-$C_8$-alkenyl, phenyl, benzyl, or —(CO)—R' or
$R^g$ and $R^h$, together with the nitrogen atom to which they are attached, form a 5- to 7-membered heterocyclic or heteroaryl ring optionally substituted with 1 or 2 OH;
R' is $NH_2$, —NH—$C_1$-$C_7$-alkyl, $C_1$-$C_7$-alkyl, or $C_1$-$C_7$-alkoxy;
m is 1 to 4; and
n is 2 to 6;
and pharmaceutically acceptable salts thereof.

In one embodiment, the invention provides compounds of formula (I)

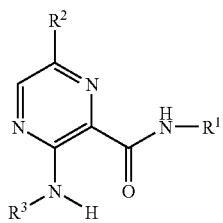

wherein
R¹ is a 5- or 6-membered ring of formula (II) or (III):

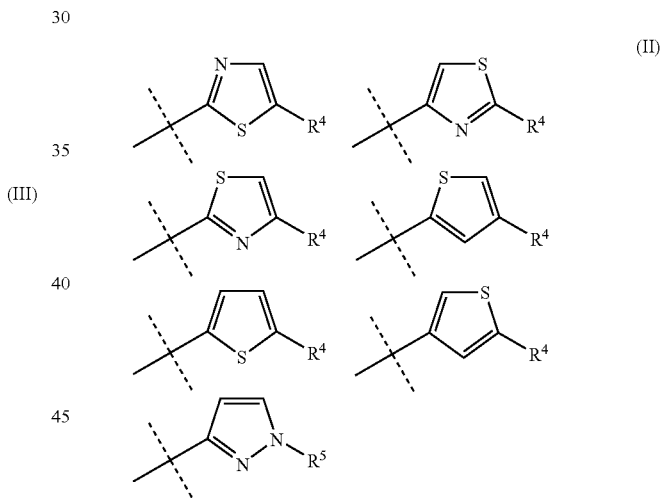

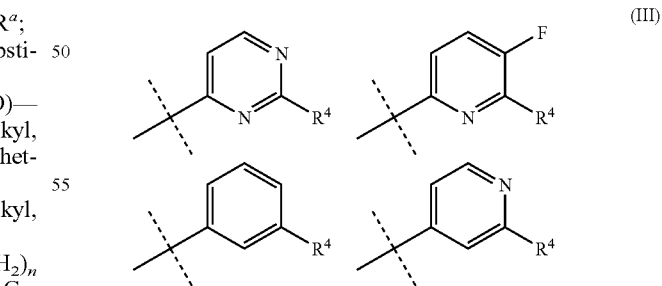

$R^2$ is H, $C_1$-$C_7$-alkyl, $C_3$-$C_6$-cycloalkyl, or —$(CH_2)_m$—$R^a$;
$R^3$ is aryl or heteroaryl each of which is optionally substituted by:
 CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —S(O)$_2$—$R^d$, or heteroaryl which is optionally substituted by $C_1$-$C_7$-alkyl;

$R^4$ is —OH, Cl, F, Br, CN, —CHF$_2$, CF$_3$, C$_1$-C$_7$-alkyl, —O—(CO)—C$_1$-C$_7$-alkyl, or —(CH$_2$)$_m$—R$^e$;

$R^5$ is C$_1$-C$_7$-alkyl, C$_1$-C$_7$-alkyl-C$_3$-C$_6$-cycloalkyl, —(CH$_2$)$_n$—O—R$^f$, C$_3$-C$_8$-alkenyl-O—R$^f$, —(CH$_2$)$_n$—NR$^g$R$^h$, —C$_2$-C$_6$-alkenyl-NR$^g$R$^h$, or —(CH$_2$)$_n$—R';

$R^a$ is —O—C$_1$-C$_7$-alkyl or —OH;

$R^b$ is C$_1$-C$_7$-alkyl, NH$_2$, or —O—C$_1$-C$_7$-alkyl;

$R^c$ is —OH, NH$_2$, or NH—(CO)—O—C$_1$-C$_7$-alkyl;

$R^d$ is C$_1$-C$_7$-alkyl, —NH$_2$, —NH—C$_1$-C$_7$-alkyl, or —N-di(C$_1$-C$_7$-alkyl);

$R^e$ is —OH, —CH$_2$F, —CHF$_2$, —CF$_3$, or —O—(CO)—C$_1$-C$_7$-alkyl;

$R^f$ is C$_1$-C$_7$-alkyl, C$_3$-C$_8$-alkenyl, C$_3$-C$_6$-cycloalkyl, phenyl, benzyl, or —(CO)—R';

$R^g$ and $R^h$ are each independently H, C$_1$-C$_7$-alkyl, C$_3$-C$_6$-cycloalkyl, C$_3$-C$_8$-alkenyl, phenyl, benzyl, or —(CO)—R' or $R^g$ and $R^h$, together with the nitrogen atom to which they are attached, form a 5- to 7-membered heterocyclic or heteroaryl ring optionally substituted with 1 or 2 OH;

R' is NH$_2$, —NH—C$_1$-C$_7$-alkyl, C$_1$-C$_7$-alkyl, or C$_1$-C$_7$-alkoxy;

m is 1 to 4; and n is 2 to 6;

and pharmaceutically acceptable salts thereof.

Also encompassed by the compounds of formula (I) are compounds of formula (Ia):

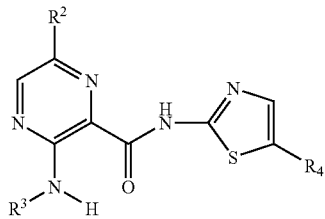

(Ia)

wherein $R^2$, $R^3$ and $R^4$ are as defined hereinabove.

In certain embodiments, the compounds of formula (Ia) according to the invention are those compounds wherein:
$R^2$ is H or C$_1$-C$_7$-alkyl;
$R^3$ is H, phenyl or 5- or 6-membered heteroaryl each of which is optionally substituted by:
  CN, Cl, F, Br, CF$_3$, CHF$_2$, —O—C$_1$-C$_7$-alkyl, —(CO)—R$^b$, —(CH$_2$)$_m$—R$^c$, —NH—(CO)—C$_1$-C$_7$-alkyl, —O—CH$_2$F, —O—CHF$_2$, —O—CF$_3$, —S(O)$_2$—R$^d$, or heteroaryl which is optionally substituted by C$_1$-C$_7$-alkyl;
$R^4$ is H, —OH, Cl, F, Br, CN, —CHF$_2$, CF$_3$, C$_1$-C$_7$-alkyl, —O—(CO)—C$_1$-C$_7$-alkyl, or —(CH$_2$)$_m$—R$^e$; and $R^b$, $R^c$, $R^d$ and $R^e$ are as defined hereinabove, as well as pharmaceutically acceptable salts thereof, for example 6-Methyl-3-(pyrimidin-5-ylamino)-pyrazine-2-carboxylic acid (1-methyl-1H-pyrazol-3-yl)-amide hydrochloride.

Further compounds encompassed by the compounds of formula (I) are compounds of formula (Ib):

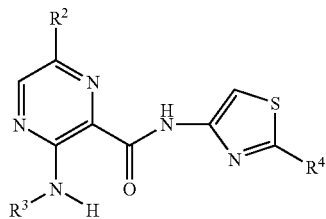

(Ib)

wherein $R^2$, $R^3$ and $R^4$ are as defined hereinabove.

In certain embodiments, the compounds of formula (Ib) according to the invention are those compounds wherein:
$R^2$ is H or C$_1$-C$_7$-alkyl;
$R^3$ is H, phenyl or 5- or 6-membered heteroaryl each of which is optionally substituted by:
  CN, Cl, F, Br, CF$_3$, CHF$_2$, —O—C$_1$-C$_7$-alkyl, —(CO)—R$^b$, —(CH$_2$)$_m$—R$^c$, —NH—(CO)—C$_1$-C$_7$-alkyl, —O—CH$_2$F, —O—CHF$_2$, —O—CF$_3$, —S(O)$_2$—R$^d$, or heteroaryl which is optionally substituted by C$_1$-C$_7$-alkyl;
$R^4$ is H, —OH, Cl, F, Br, CN, —CHF$_2$, CF$_3$, C$_1$-C$_7$-alkyl, —O—(CO)—C$_1$-C$_7$-alkyl, or —(CH$_2$)$_m$—R$^e$; and
$R^b$, $R^c$, $R^d$ and $R^e$ are as defined hereinabove, as well as pharmaceutically acceptable salts thereof, for example 6-Methyl-3-(pyrimidin-5-ylamino)-pyrazine-2-carboxylic acid (2-methyl-thiazol-4-yl)-amide hydrochloride.

Further compounds encompassed by the compounds of formula (I) are compounds of formula (Ic):

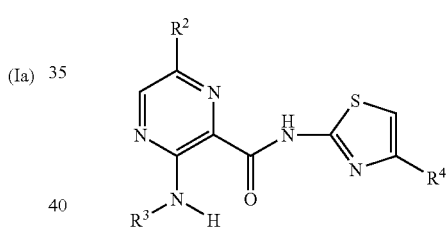

(Ic)

wherein $R^2$, $R^3$ and $R^4$ are as defined hereinabove.

In certain embodiments, the compounds of formula (Ic) according to the invention are compounds wherein:
$R^2$ is H or C$_1$-C$_7$-alkyl;
$R^3$ is H, phenyl or 5- or 6-membered heteroaryl each of which is optionally substituted by:
  CN, Cl, F, Br, CF$_3$, CHF$_2$, —O—C$_1$-C$_7$-alkyl, —(CO)—R$^b$, —(CH$_2$)$_m$—R$^c$, —NH—(CO)—C$_1$-C$_7$-alkyl, —O—CH$_2$F, —O—CHF$_2$, —O—CF$_3$, —S(O)$_2$—R$^d$, or heteroaryl which is optionally substituted by C$_1$-C$_7$-alkyl;
$R^4$ is H, —OH, Cl, F, Br, CN, —CHF$_2$, CF$_3$, C$_1$-C$_7$-alkyl, —O—(CO)—C$_1$-C$_7$-alkyl, or —(CH$_2$)$_m$—R$^e$; and
$R^b$, $R^c$, $R^d$ and $R^e$ are as defined hereinabove, as well as pharmaceutically acceptable salts thereof, for example the following compounds:
3-(3-Fluoro-phenylamino)-pyrazine-2-carboxylic acid (4-methyl-thiazol-2-yl)-amide;
3-(Pyridin-3-ylamino)-pyrazine-2-carboxylic acid (4-methyl-thiazol-2-yl)-amide dihydrochloride;
3-(Pyrimidin-5-ylamino)-pyrazine-2-carboxylic acid (4-methyl-thiazol-2-yl)-amide;
6-Methyl-3-(pyridin-3-ylamino)-pyrazine-2-carboxylic acid (4-methyl-thiazol-2-yl)-amide hydrochloride; and
6-Methyl-3-(pyrimidin-5-ylamino)-pyrazine-2-carboxylic acid (4-methyl-thiazol-2-yl)-amide.

Further compounds encompassed by the compounds of formula (I) are compounds of formula (Id):

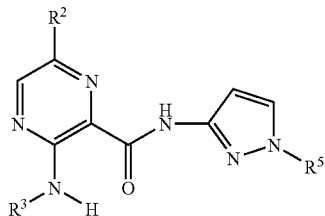

(Id)

wherein $R^2$, $R^3$ and $R^5$ are as defined hereinabove.

In certain embodiments, the compounds of formula (Id) according to the invention are those compounds wherein:
$R^2$ is H or $C_1$-$C_7$-alkyl;
$R^3$ is H, phenyl or 5- or 6-membered heteroaryl each of which is optionally substituted by:
 CN, Cl, F, Br, $CF_3$, $CHF_2$, —O—$C_1$-$C_7$-alkyl, —(CO)—$R^b$, —($CH_2$)$_m$—$R^c$, —NH—(CO)—$C_1$-$C_7$-alkyl, —O—$CH_2$F, —O—$CHF_2$, —O—$CF_3$, —S(O)$_2$—$R^d$, or heteroaryl which is optionally substituted by $C_1$-$C_7$-alkyl;
$R^5$ is H, $C_1$-$C_7$-alkyl, $C_1$-$C_7$-alkyl-$C_3$-$C_6$-cycloalkyl, —($CH_2$)$_n$—O—$R^f$, $C_3$-$C_8$-alkenyl-O—$R^f$, —($CH_2$), —NR$^g$R$^h$, —$C_2$-$C_6$-alkenyl-NR$^g$R$^h$, or —($CH_2$)$_n$—$R^e$; and
$R^b$, $R^c$, $R^d$, $R^e$, $R^f$, $R^g$ and $R^h$ are as defined hereinabove, as well as pharmaceutically acceptable salts thereof, for example the following compounds:
3-(5-Fluoro-pyridin-3-ylamino)-pyrazine-2-carboxylic acid (1-methyl-1H-pyrazol-3-yl)-amide;
6-Methyl-3-(pyridin-3-ylamino)-pyrazine-2-carboxylic acid (1-methyl-1H-pyrazol-3-yl)-amide hydrochloride; and
6-Methyl-3-(pyrimidin-5-ylamino)-pyrazine-2-carboxylic acid (1-methyl-1H-pyrazol-3-yl)-amide hydrochloride.

Further compounds encompassed by the compounds of formula (I) are compounds of formula (Ie):

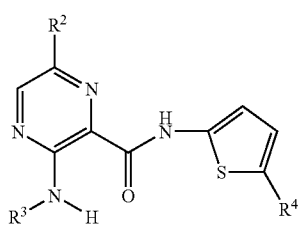

(Ie)

wherein $R^2$, $R^3$ and $R^4$ are as defined hereinabove.

In certain embodiments, the compounds of formula (Ie) according to the invention are those compounds wherein:
$R^2$ is H or $C_1$-$C_7$-alkyl;
$R^3$ is H, phenyl or 5- or 6-membered heteroaryl each of which is optionally substituted by:
 CN, Cl, F, Br, $CF_3$, $CHF_2$, —O—$C_1$-$C_7$-alkyl, —(CO)—$R^b$, —($CH_2$)$_m$—$R^c$, —NH—(CO)—$C_1$-$C_7$-alkyl, —O—$CH_2$F, —O—$CHF_2$, —O—$CF_3$, —S(O)$_2$—$R^d$, or heteroaryl which is optionally substituted by $C_1$-$C_7$-alkyl;

$R^4$ is H, —OH, Cl, F, Br, CN, —$CHF_2$, $CF_3$, $C_1$-$C_7$-alkyl, —O—(CO)—$C_1$-$C_7$-alkyl, or —($CH_2$)$_m$—$R^e$; and
$R^b$, $R^c$, $R^d$ and $R^e$ are as defined hereinabove, as well as pharmaceutically acceptable salts thereof.

Further compounds encompassed by the compounds of formula (I) are compounds of formula (If):

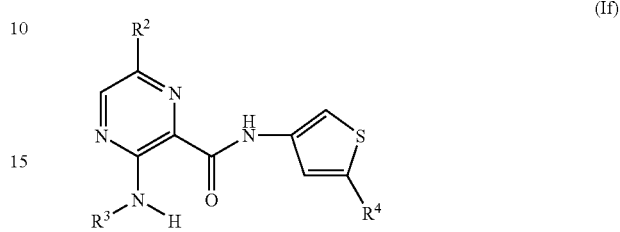

(If)

wherein $R^2$, $R^3$ and $R^4$ are as defined hereinabove.

In certain embodiments, the compounds of formula (If) according to the invention are those compounds wherein:
$R^2$ is H or $C_1$-$C_7$-alkyl;
$R^3$ is H, phenyl or 5- or 6-membered heteroaryl each of which is optionally substituted by:
 CN, Cl, F, Br, $CF_3$, $CHF_2$, —O—$C_1$-$C_7$-alkyl, —(CO)—$R^b$, —($CH_2$)$_m$—$R^c$, —NH—(CO)—$C_1$-$C_7$-alkyl, —O—$CH_2$F, —O—$CHF_2$, —O—$CF_3$, —S(O)$_2$—$R^d$, or heteroaryl which is optionally substituted by $C_1$-$C_7$-alkyl;
$R^4$ is H, —OH, Cl, F, Br, CN, —$CHF_2$, $CF_3$, $C_1$-$C_7$-alkyl, —O—(CO)—$C_1$-$C_7$-alkyl, or —($CH_2$)$_m$—$R^e$; and
$R^b$, $R^c$, $R^d$ and $R^e$ are as defined hereinabove, as well as pharmaceutically acceptable salts thereof.

Further compounds encompassed by the compounds of formula (I) are compounds of formula (Ig):

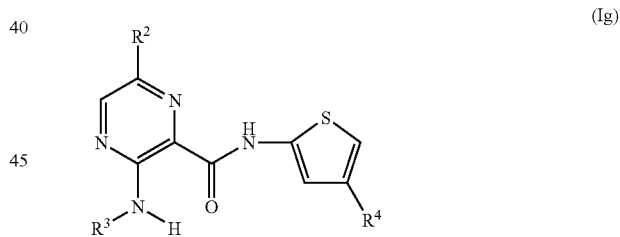

(Ig)

wherein $R^2$, $R^3$ and $R^4$ are as defined hereinabove.

In certain embodiments, the compounds of formula (Ig) according to the invention are these compounds wherein:
$R^2$ is H or $C_1$-$C_7$-alkyl;
$R^3$ is H, phenyl or 5- or 6-membered heteroaryl each of which is optionally substituted by:
 CN, Cl, F, Br, $CF_3$, $CHF_2$, —O—$C_1$-$C_7$-alkyl, —(CO)—$R^b$, —($CH_2$)$_m$—$R^c$, —NH—(CO)—$C_1$-$C_7$-alkyl, —O—$CH_2$F, —O—$CHF_2$, —O—$CF_3$, —S(O)$_2$—$R^d$, or heteroaryl which is optionally substituted by $C_1$-$C_7$-alkyl;
$R^4$ is H, —OH, Cl, F, Br, CN, —$CHF_2$, $CF_3$, $C_1$-$C_7$-alkyl, —O—(CO)—$C_1$-$C_7$-alkyl, or —($CH_2$)$_m$—$R^e$; and
$R^b$, $R^c$, $R^d$ and $R^e$ are as defined hereinabove, as well as pharmaceutically acceptable salts thereof.

Further compounds encompassed by the compounds of formula (I) are compounds of formula (Ih):

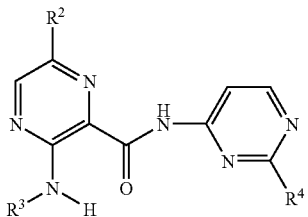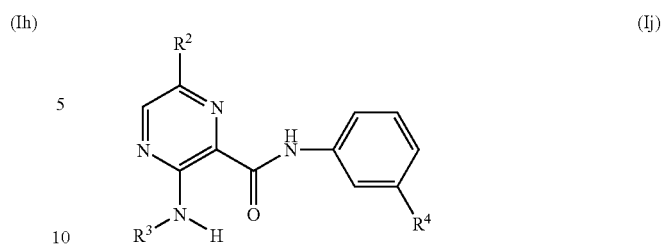

wherein $R^2$, $R^3$ and $R^4$ are as defined hereinabove.

In certain embodiments, the compounds of formula (Ih) according to the invention are those compounds wherein:

$R^2$ is H or $C_1$-$C_7$-alkyl;

$R^3$ is H, phenyl or 5- or 6-membered heteroaryl each of which is optionally substituted by:

CN, Cl, F, Br, $CF_3$, $CHF_2$, —O—$C_1$-$C_7$-alkyl, —(CO)—$R^b$, —(CH$_2$)$_m$—$R^c$, —NH—(CO)—$C_1$-$C_7$-alkyl, —O—CH$_2$F, —O—CHF$_2$, —O—CF$_3$, —S(O)$_2$—$R^d$, or heteroaryl which is optionally substituted by $C_1$-$C_7$-alkyl;

$R^4$ is H, —OH, Cl, F, Br, CN, —CHF$_2$, CF$_3$, $C_1$-$C_7$-alkyl, —O—(CO)—$C_1$-$C_7$-alkyl, or —(CH$_2$)$_m$—$R^e$; and $R^b$, $R^c$, $R^d$ and $R^e$ as defined hereinabove, as well as pharmaceutically acceptable salts thereof.

Further compounds encompassed by the compounds of formula (I) are compounds of formula (II):

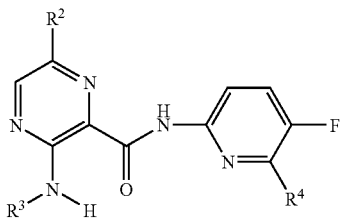

wherein $R^2$, $R^3$ and $R^4$ are as defined hereinabove. In this embodiment, $R^4$ can also be H.

In certain embodiments, the compounds of formula (II) according to the invention are compounds wherein:

$R^2$ is H or $C_1$-$C_7$-alkyl;

$R^3$ is H, phenyl or 5- or 6-membered heteroaryl each of which is optionally substituted by:

CN, Cl, F, Br, $CF_3$, $CHF_2$, —O—$C_1$-$C_7$-alkyl, —(CO)—$R^b$, —(CH$_2$)$_m$—$R^c$, —NH—(CO)—$C_1$-$C_7$-alkyl, —O—CH$_2$F, —O—CHF$_2$, —O—CF$_3$, —S(O)$_2$—$R^d$, or heteroaryl which is optionally substituted by $C_1$-$C_7$-alkyl;

$R^4$ is H, —OH, Cl, F, Br, CN, —CHF$_2$, CF$_3$, $C_1$-$C_7$-alkyl, —O—(CO)—$C_1$-$C_7$-alkyl, or —(CH$_2$)$_m$—$R^e$; and $R^b$, $R^c$, $R^d$ and $R^e$ are as defined hereinabove, as well as pharmaceutically acceptable salts thereof, for example the following compounds:

6-Methyl-3-(pyridin-3-ylamino)-pyrazine-2-carboxylic acid (5-fluoro-pyridin-2-yl)-amide hydrochloride; and 6-Methyl-3-(pyrimidin-5-ylamino)-pyrazine-2-carboxylic acid (5-fluoro-pyridin-2-yl)-amide.

Still further compounds encompassed by the compounds of formula (I) are compounds of formula (Ij):

wherein $R^2$, $R^3$ and $R^4$ are as defined hereinabove.

In certain embodiments, the compounds of formula (Ij) according to the invention are those compounds wherein:

$R^2$ is H or $C_1$-$C_7$-alkyl;

$R^3$ is H, phenyl or 5- or 6-membered heteroaryl each of which is optionally substituted by:

CN, Cl, F, Br, $CF_3$, $CHF_2$, —O—$C_1$-$C_7$-alkyl, —(CO)—$R^b$, —(CH$_2$)$_m$—$R^c$, —NH—(CO)—$C_1$-$C_7$-alkyl, —O—CH$_2$F, —O—CHF$_2$, —O—CF$_3$, —S(O)$_2$—$R^d$, or heteroaryl which is optionally substituted by $C_1$-$C_7$-alkyl;

$R^4$ is H, —OH, Cl, F, Br, CN, —CHF$_2$, CF$_3$, $C_1$-$C_7$-alkyl, —O—(CO)—$C_1$-$C_7$-alkyl, or —(CH$_2$)$_m$—$R^e$; and $R^b$, $R^c$, $R^d$ and $R^e$ are as defined hereinabove, as well as pharmaceutically acceptable salts thereof, for example the following compounds:

3-(Pyridin-3-ylamino)-pyrazine-2-carboxylic acid (3-chloro-phenyl)-amide;

3-Phenylamino-pyrazine-2-carboxylic acid (3-chloro-phenyl)-amide; and

6-Methyl-3-(pyrimidin-5-ylamino)-pyrazine-2-carboxylic acid (3-chloro-phenyl)-amide hydrochloride.

Still further compounds encompassed by the compounds of formula (I) are compounds of formula (Ik):

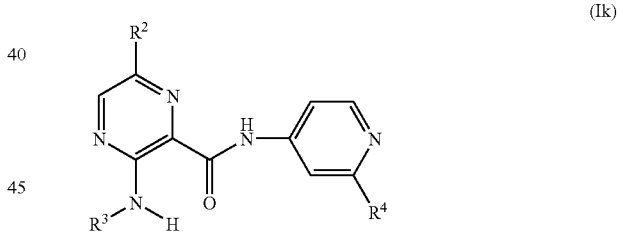

wherein $R^2$, $R^3$ and $R^4$ are as defined hereinabove.

In certain embodiments, the compounds of formula (Ik) according to the invention are compounds wherein:

$R^2$ is H or $C_1$-$C_7$-alkyl;

$R^3$ is H, phenyl or 5- or 6-membered heteroaryl each of which is optionally substituted by:

CN, Cl, F, Br, $CF_3$, $CHF_2$, —O—$C_1$-$C_7$-alkyl, —(CO)—$R^b$, —(CH$_2$)$_m$—$R^c$, —NH—(CO)—$C_1$-$C_7$-alkyl, —O—CH$_2$F, —O—CHF$_2$, —O—CF$_3$, —S(O)$_2$—$R^d$, or heteroaryl which is optionally substituted by $C_1$-$C_7$-alkyl;

$R^4$ is H, —OH, Cl, F, Br, CN, —CHF$_2$, CF$_3$, $C_1$-$C_7$-alkyl, —O—(CO)—$C_1$-$C_7$-alkyl, or —(CH$_2$)$_m$—$R^e$; and $R^b$, $R^c$, $R^d$ and $R^e$ are as defined hereinabove, as well as pharmaceutically acceptable salts thereof, for example the following compounds:

3-Phenylamino-pyrazine-2-carboxylic acid (2-methyl-pyridin-4-yl)-amide; and 3-(5-Chloro-pyridin-3-ylamino)-6-methyl-pyrazine-2-carboxylic acid (2-methyl-pyridin-4-yl)-amide.

In certain embodiments, the compounds of formula (I) are those wherein:

$R^3$ is aryl which is optionally substituted by CN, Cl, F, Br, $CHF_2$, —O—$C_1$-$C_7$-alkyl, —(CO)—$R^b$, —$(CH_2)_n$—$R^c$, —NH—(CO)—$C_1$-$C_7$-alkyl, —O—$CH_2F$, —O—$CHF_2$, —O—$CF_3$, —$S(O)_2$—$R^d$, or a heteroaryl which is optionally substituted by $C_1$-$C_7$-alkyl. In particular, compounds of formula (I) are those wherein $R^3$ is phenyl which is optionally substituted by CN, Cl, F, Br, $CHF_2$, —O—$C_1$-$C_7$-alkyl, —(CO)—$R^b$, —$(CH_2)_n$—$R^c$, —NH—(CO)—$C_1$-$C_7$-alkyl, —O—$CH_2F$, —O—$CHF_2$, —O—$CF_3$, —$S(O)_2$—$R^d$, or a heteroaryl which is optionally substituted by $C_1$-$C_7$-alkyl.

In certain embodiments, the compounds of formula (I) are those wherein:

$R^3$ is heteroaryl which is optionally substituted by CN, Cl, F, Br, $CHF_2$, —O—$C_1$-$C_7$-alkyl, —(CO)—$R^b$, —$(CH_2)_n$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl. In particular, compounds of formula (I) are those wherein $R^3$ is a 5- or 6-membered heteroaryl which is optionally substituted by CN, Cl, F, Br, $CHF_2$, —O—$C_1$-$C_7$-alkyl, —(CO)—$R^b$, —$(CH_2)_n$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl.

In certain embodiments, the compounds of formula (I) are those in which $R^f$ is $C_1$-$C_7$-alkyl, $C_3$-$C_8$-alkenyl, $C_3$-$C_6$-cycloalkyl, or —C(O)—R'. In other embodiments, compounds of formula (I) are those in which $R^f$ is phenyl or benzyl. In certain embodiments, the compounds of formula (I) are those wherein at least one of $R^g$ and $R^h$ is H, —$C_1$-$C_7$-alkyl, $C_3$-$C_6$-cycloalkyl, $C_3$-$C_8$-alkenyl, or —(CO)—R'. In other embodiments, the compounds of formula (I) are those wherein at least one of $R^g$ and $R^h$ is phenyl or benzyl. In other embodiments, the compounds of formula (I) are those wherein $R^g$ and $R^h$, together with the nitrogen atom to which they are attached, form a 5- to 7-membered heterocyclic ring optionally substituted with 1 or 2 OH. In other embodiments, the compounds of formula (I) are those wherein $R^g$ and $R^h$, together with the nitrogen atom to which they are attached, form a 5- to 7-membered heteroaryl ring optionally substituted with 1 or 2 OH.

The invention also encompasses methods for the preparation of the compounds of the invention.

The compounds of formula (I) can be prepared according to the following method of the invention which method comprises the steps of reacting an amino protected or free amino compound of formula (IVa) or (IV):

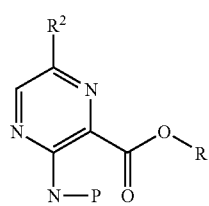

(IVa)

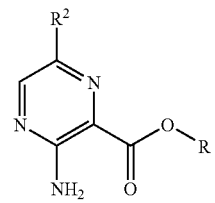

(IV)

with a compound of formula (VIII):

$$R^1—NH_2 \quad (VIII)$$

and then, if necessary, deprotecting the resulting compound to obtain a compound of formula (V):

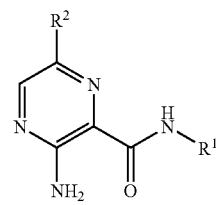

(V)

followed by reacting the compound of formula (V) with a compound of formula (IX):

$$R^3-X \quad (IX)$$

to obtain the compound of formula (I) wherein $R^1$, $R^2$ and $R^3$ are as defined hereinabove and X is halo, and R is alkyl or aralkyl (preferably methyl or ethyl).

The protecting group can be for example a carbamate protecting group such as the tert-Butoxycarbonyl (—BOC), or a bis-protected derivative such as a —(BOC)2 group.

The compounds of formula (I) can also be prepared according to the following method of the invention which method comprises the steps of reacting a compound of formula (IV):

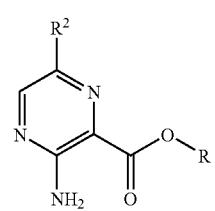

(IV)

in a diazotization reaction with sodium nitrite (or an alkyl nitrite) in presence of aqueous mineral acid H—X eventually in presence of a copper(I) salt CuX to yield a compound of formula (VI):

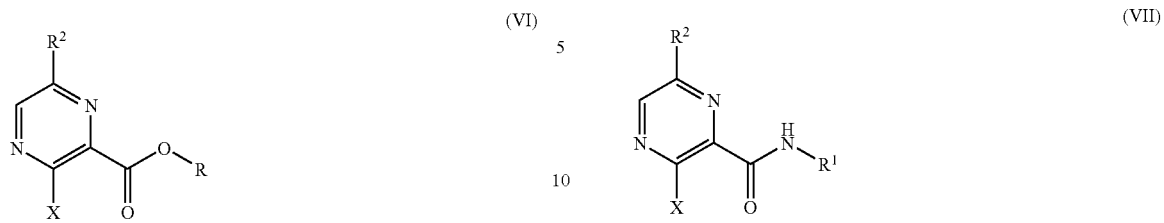

followed by reacting the compound of formula (VI) with a compound of formula (VIII):

R¹NH₂ (VIII)

to obtain a compound of formula (VII):

followed by reacting the compound of formula (VII) with a compound of formula (X):

R³—NH₂ (X)

to obtain the compound of formula (I) wherein $R^1$, $R^2$ and $R^3$ are as defined hereinabove and X is halo, and R is alkyl or aralkyl (preferably methyl or ethyl).

This method is further described in details in scheme I and general procedure I hereafter.

Scheme 1:

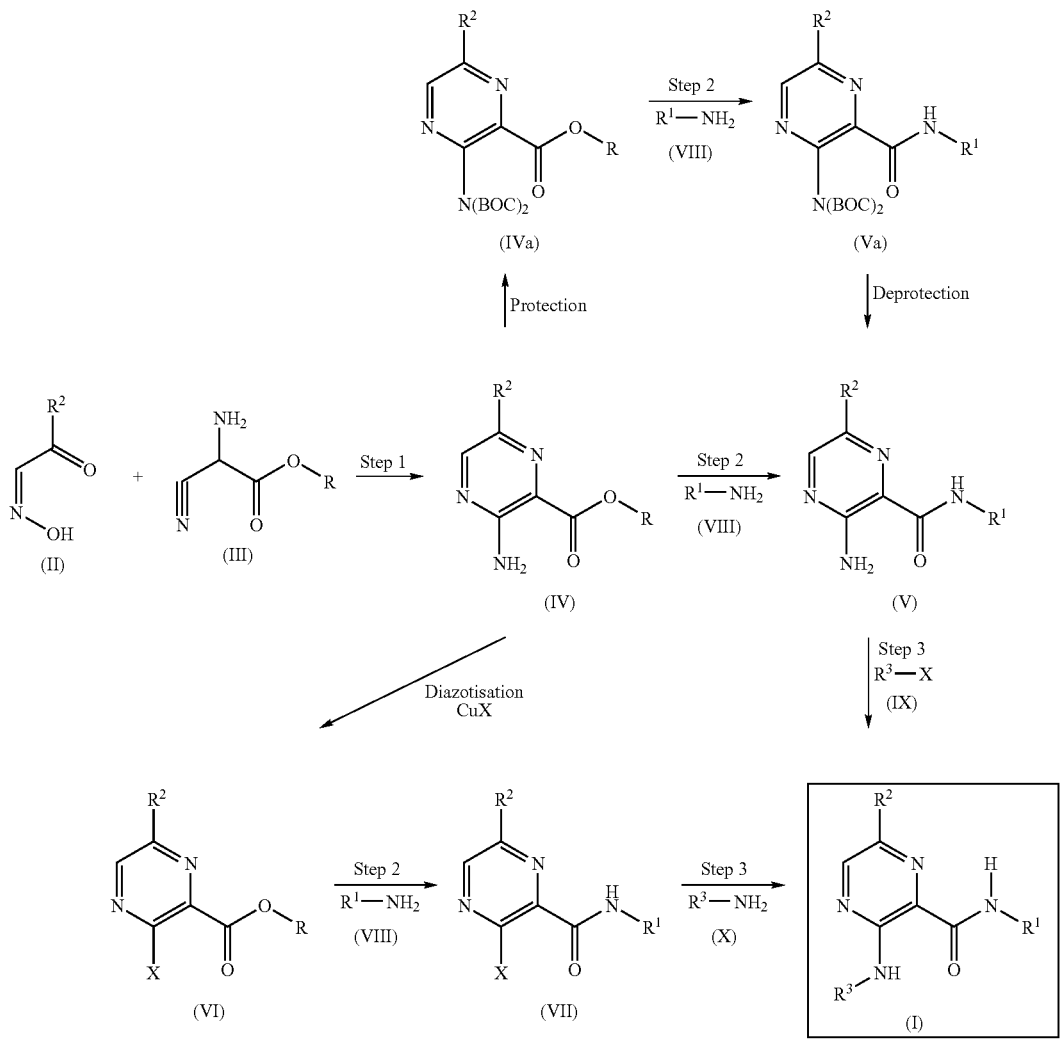

General Procedure I:

Step 1

The starting material of formula (IV) is commercially available for R²=Hydrogen. Analogs with R²=alkyl can be synthesized by condensation of the appropriate ketoaldehyde-oxime (II) with an Amino-cyano-acetic acid ester (III) [J. Med. Chem. 1997, 40, 2196-2210] in acetic acid overnight. The compound of formula (IV) can be isolated and purified using conventional methods.

Step 2

To a solution of a compound of formula (VIII) in a solvent (e.g. dry dioxane) a solution of trimethyl aluminium in hexane is added. A compound of formula (IV), (IVa), or (VI) is then added. The compounds of formula (Va), (V), or (VII) can be isolated and purified using conventional methods.

BOC-Protection

The compounds of formula (IVa) can be obtained by stirring a compound of formula (IV) with di-tert.-butyldicarbonate and 4-(N,N-dimethylamino)pyridine in refluxing dichloromethane. The compound of formula (IVa) can be isolated and purified using conventional methods.

BOC-Deprotection

The compounds of formula (V) can be obtained by stirring an acidic solution of a compound of formula (Va) in a suitable solvent (e.g. water and/or ethanol). The compound of formula (V) can be isolated and purified using conventional methods.

Step 3

The compound of formula (I) can be obtained either by a catalyzed coupling of the compound of formula (V) with a compound of formula (IX), or by coupling a compound of formula (VII) with a compound of formula (X) using e.g. Cesium carbonate, 4,5-bis(diphenylphosphino)-9,9-dimethylxanthene (Xanthphos) and tri(dibenzylidene-acetone)dipalladium chloroform complex (Pd₂(dba)₃.CHCl₃). The compound of formula (I) can then be isolated and purified using conventional methods. In certain cases for compounds of formula (IX) where X is a chlorine or a fluorine atom and R³ is a heterocyclic residue, it is also possible to conduct the coupling step in absence of a Palladium catalyst using Cesium carbonate in DMF. The compound of formula (I) can then be isolated and purified using conventional methods.

General Procedure II:

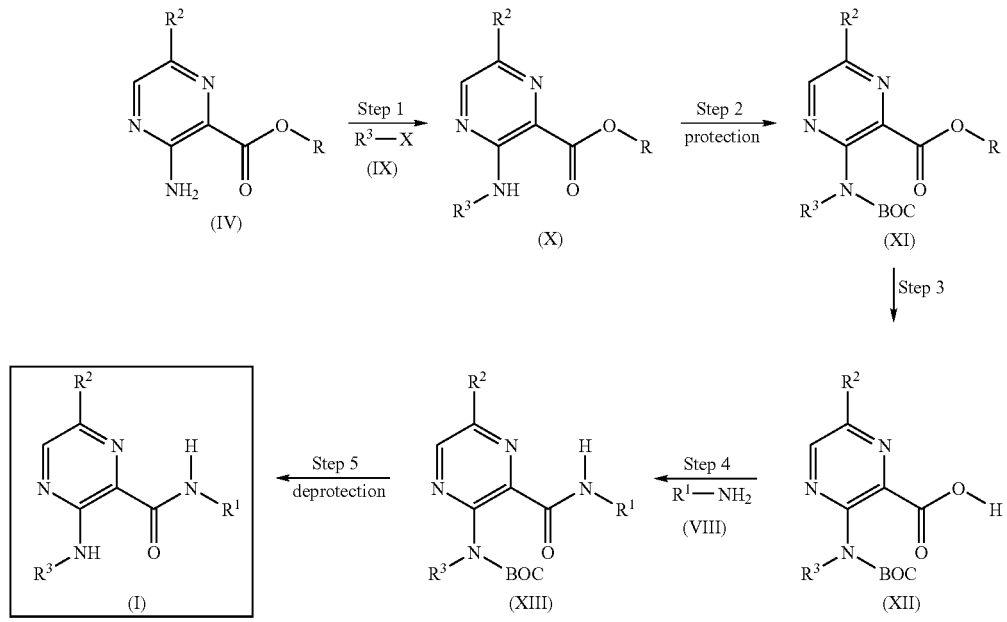

Step 1

Alternatively the compound of formula (X) can be obtained by a Pd catalyzed coupling of the compound of formula (IV) with a compound of formula (IX), using e.g. Cesium carbonate, 4,5-bis(diphenylphosphino)-9,9-dimethylxanthene (Xanthphos) and tri(dibenzylidene-acetone)dipalladium chloroform complex (Pd₂(dba)₃.CHCl₃). The compound of formula (X) can then be isolated and purified using conventional methods.

Step 2: BOC-Protection

The compounds of formula (XI) can be obtained by stirring a compound of formula (X) with di-tert.-butyldicarbonate and 4-(N,N-dimethylamino)pyridine in refluxing dichloromethane. The compound of formula (XI) can be isolated and purified using conventional methods.

Step 3: Saponification

The compounds of formula (XII) can be obtained by stirring a compound of formula (XI) with an aqueous solution of lithium hydroxide overnight at room temperature using a methanol/THF mixture as cosolvent. The compound of formula (XII) can be isolated and purified using conventional methods.

Step 4:

To a solution of a compound of formula (XII), N,N-diisopropylamine and an amine of formula (VIII) in a solvent (e.g. dry DMF) a coupling reagent (e.g. O-(benzotriazol-1-yl)-1,1,3,3-tetramethyluronium tetrafluoroborate (TBTU)) is added. After stirring overnight at room temperature, the compound of formula (XIII) can be isolated and purified using conventional methods.

Step 5: BOC-Deprotection

The compounds of formula (I) can be obtained by stirring an acidic solution of a compound of formula (XIII) in a suitable solvent (e.g. water and/or ethanol). The compound of formula (I) can be isolated and purified using conventional methods.

Pharmaceutically acceptable salts of compounds of formula I can be manufactured readily according to methods known per se and taking into consideration the nature of the compound to be converted into a salt. Inorganic or organic acids such as, for example, hydrochloric acid, hydrobromic acid, sulphuric acid, nitric acid, phosphoric acid or citric acid, formic acid, fumaric acid, maleic acid, acetic acid, succinic acid, tartaric acid, methanesulphonic acid, p-toluenesulphonic acid and the like are suitable for the formation of pharmaceutically acceptable salts of basic compounds of formula I. Compounds which contain the alkali metals or alkaline earth metals, for example sodium, potassium, calcium, magnesium or the like, basic amines or basic amino acids are suitable for the formation of pharmaceutically acceptable salts of acidic compounds.

As already mentioned above, the compounds of formula (I) and their pharmaceutically acceptable salts are, as already mentioned above, metabotropic glutamate receptor antagonists and can be used for the treatment of mGluR5 receptor mediated disorders, such as acute and/or chronic neurological disorders, cognitive disorders and memory deficits, as well as acute and chronic pain. Treatable neurological disorders are, for instance, epilepsy, schizophrenia, anxiety, acute, traumatic or chronic degenerative processes of the nervous system, such as Alzheimer's disease, senile dementia, Huntington's chorea, ALS, multiple sclerosis, dementia caused by AIDS, eye injuries, retinopathy, idiopathic parkinsonism or parkinsonism caused by medicaments as well as conditions which lead to glutamate-deficient functions, such as e.g. muscle spasms, convulsions, migraine, urinary incontinence, ethanol addiction, nicotine addiction, psychoses, opiate addiction, anxiety, vomiting, dyskinesia and depression. Other treatable indications are restricted brain function caused by bypass operations or transplants, poor blood supply to the brain, spinal cord injuries, head injuries, hypoxia caused by pregnancy, cardiac arrest and hypoglycaemia. Furthermore restricted brain function leading to mental retardation due to abnormalities during pregnancy, retarded brain development or genetic anomalies such as Fragile-X syndrome, Down syndrome, or Autism spectrum disorders such as Kanner's syndrome, Pervasive developmental disorder (PDD), Attention deficit disorder (ADD) are also possible treatable indications.

The compounds of formula I and their pharmaceutically acceptable salts are especially useful as analgesics. Treatable kinds of pain include inflammatory pain such as arthritis and rheumatoid disease, vasculitis, neuropathic pain such as trigeminal or herpetic neuralgia, diabetic neuropathy pain, causalgia, hyperalgesia, severe chronic pain, post-operative pain and pain associated with various conditions like cancer, angina, renal or billiay colic, menstruation, migraine and gout.

The pharmacological activity of the compounds was tested using the following method: For binding experiments, cDNA encoding human mGlu 5a receptor was transiently transfected into EBNA cells using a procedure described by Schlaeger and Christensen [Cytechnology 15:1-13 (1998)]. Cell membrane homogenates were stored at −80° C. until the day of assay where upon they were thawed and resuspended and polytronized in 15 mM Tris-HCl, 120 mM NaCl, 100 mM KCl, 25 mM CaCl$_2$, 25 mM MgCl$_2$ binding buffer at pH 7.4 to a final assay concentration of 20 μg protein/well.

Saturation isotherms were determined by addition of twelve [$^3$H]MPEP concentrations (0.04-100 nM) to these membranes (in a total volume of 200 μl) for 1 h at 4° C. Competition experiments were performed with a fixed concentration of [$^3$H]MPEP (2 nM), and IC$_{50}$ values of test compounds evaluated using 11 concentrations (0.3-10,000 nM). Incubations were performed for 1 h at 4° C.

At the end of the incubation, membranes were filtered onto unifilter (96-well white microplate with bonded GF/C filter preincubated 1 h in 0.1% PEI in wash buffer, Packard BioScience, Meriden, Conn.) with a Filtermate 96 harvester (Packard BioScience) and washed 3 times with cold 50 mM Tris-HCl, pH 7.4 buffer. Nonspecific binding was measured in the presence of 10 μM MPEP. The radioactivity on the filter was counted (3 min) on a Packard Top-count microplate scintillation counter with quenching correction after addition of 45 μl of microscint 40 (Canberra Packard S.A., Zürich, Switzerland) and shaking for 20 min.

For functional assays, [Ca$^{2+}$]i measurements were performed as described previously by Porter et al. [Br. J. Pharmacol. 128:13-20 (1999)] on recombinant human mGlu 5a receptors in HEK-293 cells. The cells were dye loaded using Fluo 4-AM (obtainable by FLUKA, 0.2 μM final concentration). [Ca$^{2+}$]i measurements were performed using a fluorometric imaging plate reader (FLIPR, Molecular Devices Corporation, La Jolla, Calif., USA). Antagonist evaluation was performed following a 5 min preincubation with the test compounds followed by the addition of a submaximal addition of agonist.

The inhibition (antagonists) curves were fitted with a four parameter logistic equation giving IC$_{50}$, and Hill coefficient using iterative non linear curve fitting software (Xcel fit).

For binding experiments the Ki values of the compounds tested are given. The Ki value is defined by the following formula:

$$K_i = IC_{50}/[1+L/K_d]$$

in which the IC$_{50}$ values are these concentrations of the compounds tested which cause 50% inhibition of the competing radioligand ([$^3$H]MPEP). L is the concentration of radioligand used in the binding experiment and the K$_d$ value of the radioligand is empirically determined for each batch of membranes prepared.

The compounds of the present invention are mGluR 5a receptor antagonists. The activities of compounds of formula I as measured in the assay described above are in the range of K$_i$<4 μM and preferably <150 nM.

| Example No. | Ki nM |
|---|---|
| 1 | 54 |
| 2 | 95 |
| 3 | 71 |
| 4 | 761 |
| 5 | 1628 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragees, hard and soft gelatin capsules, solutions, emulsions, or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula I, but as a rule are not necessary. Suitable carriers for suppositories are, for example, natural or hardened oils, waxes, fats, semi-liquid or liquid polyols and the like.

In addition, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable salts thereof and, if desired, one or more other therapeutically valuable substances into a galenical administration form together with one or more therapeutically inert carriers.

The present invention further provides methods for the treatment of mGluR5 mediated disorders. In particular, the invention provides a method for treating a disorder selected from the group consisting of acute and/or chronic neurological disorders, anxiety, behavioral disorders, and obsessive compulsive disorders (OCD). The invention also provides a method for treating a disorder selected from the group consisting of anorexia and bulimia. The invention further provides a method for treating a disorder selected from the group consisting of schizophrenia, Alzheimer's disease, and Parkinson's disease. Such methods comprise administering to an individual a therapeutically effective amount of a compound of the invention and a pharmaceutically acceptable carrier.

The dosage at which compounds of the invention can be administered can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

The following examples are provided to further elucidate the invention and are not intended to limit the invention to the sole compounds exemplified:

Example 1

3-(Pyridin-3-ylamino)-pyrazine-2-carboxylic acid (3-chloro-phenyl)-amide

Step 1: 3-(Pyridin-3-ylamino)-pyrazine-2-carboxylic acid methyl ester

3-Aminopyrazine-2-carboxylic acid methyl ester (0.8 g, 5.2 mmol) and 3-bromopyridine (1.2 g, 7.8 mmol) were dissolved in 20 mL dry toluene. 4,5-bis(diphenylphosphino)-9,9-dimethylxanthene (0.6 g, 1.04 mmol), sodium tert.-butylate (0.75 g, 7.8 mmol) and tri(dibenzylideneacetone)dipalladium chloroform complex (0.54 g, 0.52 mmol) were added and the reaction mixture was stirred under microwave irradiation for 60 minutes at 150° C. The reaction mixture was then evaporated and purified by flash chromatography on silica gel (heptane/ethyl acetate 1:2->0:100 gradient). The desired product was obtained as a brown solid (260 mg, 22%), MS: m/e=231.1 (M+H$^+$).

Step 2: 3-(Pyridin-3-ylamino)-pyrazine-2-carboxylic acid (3-chloro-phenyl)-amide 3-Chloroaniline (140 mg, 1.1 mmol) was dissolved in 4 mL dioxane and trimethylaluminium-solution 2M in heptane (0.55 mL, 1.1 mmol) was added. The solution was stirred for 1 hr at room temperature and 3-(pyridin-3-ylamino)-pyrazine-2-carboxylic acid methyl ester (127 mg, 0.55 mmol) was added. The reaction mixture was stirred for 2 hrs at 80° C., cooled and quenched with 0.5 mL water. Sodium sulfate was added, stirred for 10 minutes, filtered and evaporated. The crude product was purified by flash chromatography on silica gel (heptane/ethyl acetate 1:2->0:100 gradient) and the desired product was obtained as a yellow solid (13 mg, 7.2%), MS: m/e=326.2 (M+H$^+$).

Example 2

3-Phenylamino-pyrazine-2-carboxylic acid (3-chloro-phenyl)-amide

Step 1: 3-Phenylamino-pyrazine-2-carboxylic acid methyl ester

The title compound, MS: m/e=230.3 (M+H$^+$), was isolated as a byproduct of example 1, step 1.

Step 2: 3-Phenylamino-pyrazine-2-carboxylic acid (3-chloro-phenyl)-amide

The title compound, MS: m/e=325.1 (M+H$^+$), was prepared in accordance with the general method of example 1, step 2 from 3-phenylamino-pyrazine-2-carboxylic acid methyl ester and 3-chloroaniline.

Example 3

3-(5-Fluoro-pyridin-3-ylamino)-pyrazine-2-carboxylic acid (1-methyl-1H-pyrazol-3-yl)-amide Step 1: 3-Di-(tert-butoxycarbonyl)amino-pyrazine-2-carboxylic acid methyl ester 3-Aminopyrazine-2-carboxylic acid methyl ester (2.5 g, 16.3 mmol), di-tert.-butyldicarbonate (7.5 g, 34.4 mmol) and 4-(N,N-dimethylamino)pyridine (0.1 g, 0.8 mmol) were dissolved in 100 mL dichloromethane and refluxed for 4 hrs. The reaction mixture was cooled and extracted with sat. NaHCO$_3$— solution and ethyl acetate. The organic extract was dried with sodium sulfate, filtered and evaporated. The crude product was purified by flash chromatography on silica gel (heptane/ethyl acetate 90:10->1:1 gradient). The desired compound was obtained as a white solid (4.7 g, 81%), MS: m/e=354.0 (M+H$^+$).

Step 2: [3-(1-Methyl-1H-pyrazol-3-ylcarbamoyl)-pyrazin-2-yl]-carbamic acid di-tert-butyl ester The title compound, MS: m/e=219.2 (M+H$^+$), was prepared in accordance with the general method of example 1, step 2 from 3-di-(tert-butoxycarbonyl)amino-pyrazine-2-carboxylic acid methyl ester and 1-methyl-1H-pyrazol-3-ylamine [Synthesis 1976 Page 52].

Step 3: 3-Amino-pyrazine-2-carboxylic acid (1-methyl-1H-pyrazol-3-yl)-amide hydrochloride

[3-(1-Methyl-1H-pyrazol-3-ylcarbamoyl)-pyrazin-2-yl]-carbamic acid di-tert-butyl ester (0.65 g, 1.55 mmol) was dissolved in 10 mL ethyl acetate and 8M HCl in ethanol (3.9 mL, 31 mmol) was added. The reaction mixture was stirred for 3 hrs at room temperature and diluted then with 20 mL diisopropylether. The solid material was filtered off and dried at 50° C. and 15 mbar for 1 hr. The desired compound was obtained as a yellow solid (0.37 g, 94%), MS: m/e 219.3 (M+H+).

Step 4: 3-(5-Fluoro-pyridin-3-ylamino)-pyrazine-2-carboxylic acid (1-methyl-1H-pyrazol-3-yl)-amide 3-Amino-pyrazine-2-carboxylic acid (1-methyl-1H-pyrazol-3-yl)-amide hydrochloride (120 mg, 0.47 mmol), 3,5-difluoropyridine (500 mg, 4.4 mmol), cesium carbonate (610 mg, 1.89 mmol) and 1 mL N,N-dimethylformamide were mixed and stirred under microwave irradiation for 60 minutes at 180° C. The reaction mixture was extracted with sat. $NaHCO_3$— solution and three times ethyl acetate. The combined organic extracts were dried with sodium sulfate, filtered and evaporated. The crude product was purified by flash chromatography on silica gel (heptane/ethyl acetate 90:10->30:70 gradient). The desired compound was obtained as a yellow solid (24 mg, 16%), MS: m/e=314.0 (M+H$^+$).

Example 4

3-Phenylamino-pyrazine-2-carboxylic acid (2-methyl-pyridin-4-yl)-amide

Step 1: 3-Bromo-pyrazine-2-carboxylic acid (2-methyl-pyridin-4-yl)-amide

The title compound, MS: m/e=294.9 (M+H$^+$), was prepared in accordance with the general method of example 1, step 2 from 3-bromo-pyrazine-2-carboxylic acid methyl ester (Example A) and 2-methyl-pyridin-4-ylamine (Example B).

Step 2: 3-Phenylamino-pyrazine-2-carboxylic acid (2-methyl-pyridin-4-yl)-amide

3-Bromo-pyrazine-2-carboxylic acid (2-methyl-pyridin-4-yl)-amide (130 mg, 0.44 mmol) and aniline (54 mg, 0.58 mmol) were dissolved in 4 mL dry dioxane. 4,5-bis(diphenylphosphino)-9,9-dimethylxanthene (51 mg, 0.09 mmol), cesium carbonate (290 mg, 0.89 mmol) and tri(dibenzylideneacetone)dipalladium chloroform complex (46 mg, 0.044 mmol) were added and the reaction mixture was stirred under microwave irradiation for 50 minutes at 150° C. The reaction mixture was then evaporated and purified by flash chromatography on silica gel (heptane/ethyl acetate 1:1->100% ethyl acetate). The desired product was obtained as a yellow solid (47 mg, 35%), MS: m/e=306.2 (M+H$^+$).

Example 5

3-(5-Chloro-pyridin-3-ylamino)-6-methyl-pyrazine-2-carboxylic acid (2-methyl-pyridin-4-yl)-amide Step 1: 3-Bromo-6-methyl-pyrazine-2-carboxylic acid ethyl ester A mixture of 3-amino-6-methyl-pyrazine-2-carboxylic acid ethyl ester (Example C) (2.0 g, 11 mmol), 4 mL water and 3.7 mL (33.1 mmol) hydrobromic acid 48% was cooled to 5° C. 2.5M $NaNO_2$— solution in water (5.3 mL, 13.2 mmol) was added drop wise at 5° C. ($N_2$-evolution!). The reaction mixture was stirred for 1 hr and poured then into ice-water. The reaction mixture was neutralized with $Na_2CO_3$ and extracted two times with ethyl acetate (200 mL each). The combined organic extracts were dried with sodium sulfate, filtered and evaporated. The crude product was purified by flash chromatography on silica gel (heptane/ethyl acetate 90:10->50:50 gradient). The desired compound was obtained as a colorless liquid (0.53 g, 20%), MS: m/e 245.1 (M+H$^+$).

Step 2: 3-Bromo-6-methyl-pyrazine-2-carboxylic acid (2-methyl-pyridin-4-yl)-amide The title compound, MS: m/e=307.2 (M+H$^+$), was prepared in accordance with the general method of example 1, step 2 from 3-bromo-6-methyl-pyrazine-2-carboxylic acid ethyl ester and 2-methyl-pyridin-4-ylamine (Example B).

Step: 3-(5-Chloro-pyridin-3-ylamino)-6-methyl-pyrazine-2-carboxylic acid (2-methyl-pyridin-4-yl)-amide The title compound, MS: m/e=355.1 (M+H$^+$), was prepared in accordance with the general method of example 4, step 2 from 3-bromo-6-methyl-pyrazine-2-carboxylic acid (2-methyl-pyridin-4-yl)-amide and 5-chloropyridine-3-amine.

Example 6

3-(3-Fluoro-phenylamino)-pyrazine-2-carboxylic acid (4-methyl-thiazol-2-yl)-amide Step 1: 3-Bromo-pyrazine-2-carboxylic acid (4-methyl-thiazol-2-yl)-amide The title compound, MS: m/e=301.0 (M+H$^+$), was prepared in accordance with the general method of example 1, step 2 from 3-bromo-pyrazine-2-carboxylic acid methyl ester (Example A) and 2-amino-4-methylthiazole.

Step 2: 3-(3-Fluoro-phenylamino)-pyrazine-2-carboxylic acid (4-methyl-thiazol-2-yl)-amide The title compound, MS: m/e=330.1 (M+H$^+$), was prepared in accordance with the general method of example 4, step 2 from 3-bromo-pyrazine-2-carboxylic acid (4-methyl-thiazol-2-yl)-amide and 3-fluoroaniline.

Example 7

3-(Pyridin-3-ylamino)-pyrazine-2-carboxylic acid (4-methyl-thiazol-2-yl)-amide dihydrochloride Step 1: 3-(tert-Butoxycarbonyl-pyridin-3-yl-amino)-pyrazine-2-carboxylic acid methyl ester 3-(Pyridin-3-ylamino)-pyrazine-2-carboxylic acid methyl ester (Example 1, step 1) (245 mg, 1.06 mmol), di-tert.-butyldicarbonate (255 mg, 1.17 mmol) and 4-(N,N-dimethylamino)pyridine (7 mg, 0.05 mmol) were dissolved in 100 ml dichloromethane and refluxed for 2 hrs. The reaction mixture was cooled and extracted with sat. $NaHCO_3$— solution and ethyl acetate. The organic extract was dried with sodium sulfate, filtered and evaporated. The desired compound was obtained as a brown oil (364 mg, >100%), MS: m/e=331.3 (M+H$^+$), which was used for the next step without further purification.

Step 2: 3-(tert-Butoxycarbonyl-pyridin-3-yl-amino)-pyrazine-2-carboxylic acid 3-(tert-Butoxycarbonyl-pyridin-3-yl-amino)-pyrazine-2-carboxylic acid methyl ester (364 mg, 1.1 mmol) was dissolved in 10 ml THF. 5 ml methanol, 5 ml water and lithium hydroxide hydrate (139 mg, 3.30 mmol) were added and stirred over night at room temperature. The organic solvent was evaporated and the residue was neutralized with 2N HCl-solution. The mixture was evaporated to dryness and used without further purification for the next step [(405 mg, >100%), MS: m/e=315.2 (M+H−)].

Step 3: [3-(4-Methyl-thiazol-2-ylcarbamoyl)-pyrazin-2-yl]-pyridin-3-yl-carbamic acid tert-butyl ester 3-(tert-Butoxycarbonyl-pyridin-3-yl-amino)-pyrazine-2-carboxylic acid (405 mg, 80%, 1.02 mmol), 2-amino-4-methylthiazole (129 mg, 1.12 mmol), N,N-diisopropylethylamine (0.23 ml, 1.33 mmol) and TBTU (430 mg, 1.33 mmol) were dissolved in 1 ml DMF and stirred over night at room temperature. The reaction mixture was quenched with water and extracted two times with ethyl acetate. The organic extracts were washed with 2N NaOH-solution, water and brine, dried with sodium sulfate, filtered and evaporated. The crude product was purified by flash chromatography on silica gel (heptane/ethyl acetate 90:10->40:60 gradient). The desired compound was obtained as a yellow foam (195 mg, 46%), MS: m/e=413.3 (M+H$^+$).

Step 4: 3-(Pyridin-3-ylamino)-pyrazine-2-carboxylic acid (4-methyl-thiazol-2-yl)-amide dihydrochloride

[3-(4-Methyl-thiazol-2-ylcarbamoyl)-pyrazin-2-yl]-pyridin-3-yl-carbamic acid tert-butyl ester (180 mg, 0.44 mmol) was dissolved in 5 ml ethyl acetate and 8M HCl in ethanol (2.2 ml, 17.6 mmol) was added. The reaction mixture was stirred for 3 hrs at room temperature and diluted then with 20 mL diisopropylether. The solid material was filtered off and dried at 50° C. and 15 mbar for 1 hr. The desired compound was obtained as a yellow solid (169 mg, 99%), MS: m/e=313.1 (M+H$^+$).

Example 8

3-(Pyrimidin-5-ylamino)-pyrazine-2-carboxylic acid (4-methyl-thiazol-2-yl)-amide Step 1: 3-(Pyrimidin-5-ylamino)-pyrazine-2-carboxylic acid methyl ester The title compound, MS: m/e=232.1 (M+H$^+$), was prepared in accordance with the general method of example 4, step 2 from 3-aminopyrazine-2-carboxylic acid methyl ester and 5-bromopyrimidine.

Step 2: 3-(Pyrimidin-5-ylamino)-pyrazine-2-carboxylic acid (4-methyl-thiazol-2-yl)-amide The title compound, MS: m/e=314.0 (M+H$^+$), was prepared in accordance with the general method of example 1, step 2 from 3-(pyrimidin-5-ylamino)-pyrazine-2-carboxylic acid methyl ester and 2-amino-4-methylthiazole.

Example 9

6-Methyl-3-(pyridin-3-ylamino)-pyrazine-2-carboxylic acid (5-fluoro-pyridin-2-yl)-amide hydrochloride Step 1: 6-Methyl-3-(pyridin-3-ylamino)-pyrazine-2-carboxylic acid ethyl ester 3-Amino-6-methyl-pyrazine-2-carboxylic acid ethyl ester (Example C) (800 mg, 4.4 mmol) and 3-iodopyridine (1.63 g, 8.0 mmol) were dissolved in 17 ml dry dioxane. 4,5-bis(diphenylphosphino)-9,9-dimethylxanthene (510 mg, 0.88 mmol), cesium carbonate (2.30 g, 7.0 mmol) and tri(dibenzylideneacetone)dipalladium chloroform complex (460 mg, 0.44 mmol) were added and the reaction mixture was stirred for 16 hours at 130° C. The reaction mixture was then evaporated and purified by flash chromatography on silica gel (heptane/ethyl acetate 9:1->heptane/ethyl acetate 1:2). The desired product was obtained as a yellow oil (455 mg, 40%), MS: m/e=259.2 (M+H$^+$).

Step 2: 3-(tert-Butoxycarbonyl-pyridin-3-yl-amino)-6-methyl-pyrazine-2-carboxylic acid ethyl ester The title compound, MS: m/e=359.1 (M+H$^+$), was prepared in accordance with the general method of example 8, step 1 from 6-methyl-3-(pyridin-3-ylamino)-pyrazine-2-carboxylic acid ethyl ester.

Step 3: 3-(tert-Butoxycarbonyl-pyridin-3-yl-amino)-6-methyl-pyrazine-2-carboxylic acid The title compound, MS: m/e=329.1 (M+H−), was prepared in accordance with the general method of example 8, step 2 from 3-(tert-butoxycarbonyl-pyridin-3-yl-amino)-6-methyl-pyrazine-2-carboxylic acid ethyl ester.

Step 4: [3-(5-Fluoro-pyridin-2-ylcarbamoyl)-5-methyl-pyrazin-2-yl]-pyridin-3-yl-carbamic acid tert-butyl ester The title compound, MS: m/e=425.2 (M+H$^+$), was prepared in accordance with the general method of example 8, step 3 from 3-(tert-butoxycarbonyl-pyridin-3-yl-amino)-6-methyl-pyrazine-2-carboxylic acid and 2-amino-5-fluoropyridine.

Step 5: 6-Methyl-3-(pyridin-3-ylamino)-pyrazine-2-carboxylic acid (5-fluoro-pyridin-2-yl)-amide hydrochloride The title compound, MS: m/e=325.2 (M+H$^+$), was prepared in accordance with the general method of example 8, step 4 from [3-(5-fluoro-pyridin-2-ylcarbamoyl)-5-methyl-pyrazin-2-yl]-pyridin-3-yl-carbamic acid tert-butyl ester.

Example 10

6-Methyl-3-(pyridin-3-ylamino)-pyrazine-2-carboxylic acid (4-methyl-thiazol-2-yl)-amide hydrochloride The title compound, MS: m/e=327.1 (M+H$^+$), was prepared in accordance with the general method of example 10 from 3-(tert-butoxycarbonyl-pyridin-3-yl-amino)-6-methyl-pyrazine-2-carboxylic acid and 2-amino-4-methylthiazole.

Example 11

6-Methyl-3-(pyridin-3-ylamino)-pyrazine-2-carboxylic acid (1-methyl-1H-pyrazol-3-yl)-amide hydrochloride The title compound, MS: m/e=310.3 (M+H$^+$), was prepared in accordance with the general method of example 10 from 3-(tert-butoxycarbonyl-pyridin-3-yl-amino)-6-methyl-pyrazine-2-carboxylic acid and 1-methyl-1H-pyrazol-3-ylamine [Synthesis 1976 Page 52].

Example 12

6-Methyl-3-(pyrimidin-5-ylamino)-pyrazine-2-carboxylic acid (3-chloro-phenyl)-amide hydrochloride The title compound, MS: m/e=341.2 (M+H⁺), was prepared in accordance with the general method of example 10 from 3-amino-6-methyl-pyrazine-2-carboxylic acid ethyl ester (Example C), 5-bromopyrimidine and 3-chloroaniline.

Example 13

6-Methyl-3-(pyrimidin-5-ylamino)-pyrazine-2-carboxylic acid (5-fluoro-pyridin-2-yl)-amide The title compound, MS: m/e=326.3 (M+H⁺), was prepared in accordance with the general method of example 10 from 3-amino-6-methyl-pyrazine-2-carboxylic acid ethyl ester (Example C), 5-bromopyrimidine and 2-amino-5-fluoropyridine.

Example 14

6-Methyl-3-(pyrimidin-5-ylamino)-pyrazine-2-carboxylic acid (1-methyl-1H-pyrazol-3-yl)-amide hydrochloride The title compound, MS: m/e=311.2 (M+H⁺), was prepared in accordance with the general method of example 10 from 3-amino-6-methyl-pyrazine-2-carboxylic acid ethyl ester (Example C), 5-bromopyrimidine and 1-methyl-1H-pyrazol-3-ylamine [Synthesis 1976 Page 52].

Example 15

6-Methyl-3-(pyrimidin-5-ylamino)-pyrazine-2-carboxylic acid (2-methyl-thiazol-4-yl)-amide hydrochloride The title compound, MS: m/e=328.1 (M+H⁺), was prepared in accordance with the general method of example 10 from 3-amino-6-methyl-pyrazine-2-carboxylic acid ethyl ester (Example C), 5-bromopyrimidine and 4-amino-2-methylthiazole (Example D).

Example 16

6-Methyl-3-(pyrimidin-5-ylamino)-pyrazine-2-carboxylic acid (4-methyl-thiazol-2-yl)-amide The title compound, MS: m/e=328.3 (M+H⁺), was prepared in accordance with the general method of example 10 from 3-amino-6-methyl-pyrazine-2-carboxylic acid ethyl ester (Example C), 5-bromopyrimidine and 2-amino-4-methylthiazole

Synthesis of Intermediates

Example A

3-Bromo-pyrazine-2-carboxylic acid methyl ester

The title compound, MS: m/e=218.9 (M+H⁺), was prepared from methyl 3-aminopyrazine-2-carboxylate as described in literature by a Sandmeyer reaction.

Example B

2-Methyl-pyridin-4-ylamine

The title compound was prepared by hydrogenation of 4-nitro-2-picoline N-oxide as described in literature.

Example C

3-Amino-6-methyl-pyrazine-2-carboxylic acid ethyl ester

Step 1:
3-Amino-6-methyl-4-oxy-pyrazine-2-carboxylic acid ethyl ester

Amino-cyano-acetic acid ethyl ester (11.2 g, 87.3 mmol) [J. Med. Chem. 1997, 40, 2196-2210] was dissolved in 50 ml acetic acid and a solution of pyruvaldehyde-1-oxime (10.4 g, 119.4 mmol) in 50 ml acetic acid was added drop wise at room temperature (exothermic!->ice-bath cooling). The dark brown mixture was stirred over night at room temperature and quenched then with 100 ml water. The reaction mixture was evaporated and extracted with two times water (100 ml each) and three times ethyl acetate (200 ml each). The combined organic extracts were dried with sodium sulfate, filtered and evaporated. The crude product was purified by flash chromatography on silica gel (heptane/ethyl acetate 90:10->0:100 gradient). The desired compound was obtained as a yellow solid (7.1 g, 30%), MS: m/e=198.2 (M+H⁺).

Step 2: 3-Amino-6-methyl-pyrazine-2-carboxylic acid ethyl ester

3-Amino-6-methyl-4-oxy-pyrazine-2-carboxylic acid ethyl ester (7.1 g, 36 mmol) was dissolved in 350 ml ethanol and hydrogenated with Raney nickel for 3 hrs at room temperature. The reaction mixture was filtered and evaporated. The desired crude product was obtained as a light brown solid and used without any further purification for the next step (6.6 g, 100%), MS: m/e=182.1 (M+H⁺).

Example D

4-Amino-2-methylthiazole

The title compound can be prepared in accordance with the preparation described in patent EP 321115.

Preparation of Pharmaceutical Compositions Comprising Compounds of the Invention

Example I

Tablets of the following composition are produced in a conventional manner:

|  | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

Example II

Tablets of the following composition are produced in a conventional manner:

|  | mg/Tablet |
|---|---|
| Active ingredient | 200 |
| Powdered. lactose | 100 |
| White corn starch | 64 |
| Polyvinylpyrrolidone | 12 |
| Na carboxymethylstarch | 20 |
| Magnesium stearate | 4 |
| Tablet weight | 400 |

Example III

Capsules of the following composition are produced:

|  | mg/Capsule |
|---|---|
| Active ingredient | 50 |
| Crystalline. lactose | 60 |
| Microcrystalline cellulose | 34 |
| Talc | 5 |
| Magnesium stearate | 1 |
| Capsule fill weight | 150 |

The active ingredient having a suitable particle size, the crystalline lactose and the microcrystalline cellulose are homogeneously mixed with one another, sieved and thereafter talc and magnesium stearate are admixed. The final mixture is filled into hard gelatine capsules of suitable size.

The invention claimed is:

1. A compound of formula (I)

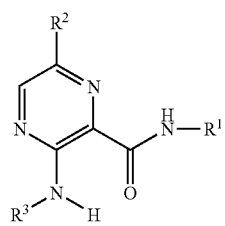

wherein
R$^1$ is a 5-ring selected from the group consisting of formulae (IIa), (IIb), (IIc), (IId), (IIe), (IIf), and (IIg):

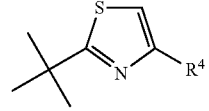

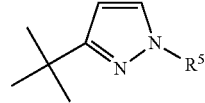

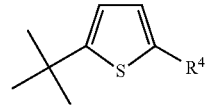

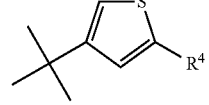

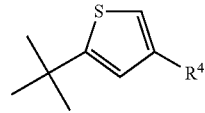

(IIf)

(IIg)

R$^2$ is H, C$_3$-C$_6$-cycloalkyl, or —(CH$_2$)$_m$—R$^a$;

R$^3$ is aryl, or heteroaryl each of which is optionally substituted by:
CN, Cl, F, Br, CF$_3$, CHF$_2$, —O—C$_1$-C$_7$-alkyl, —(CO)—R$^b$, —(CH$_2$)$_m$—R$^c$, —NH—(CO)—C$_1$-C$_7$-alkyl, —O—CH$_2$F, —O—CHF$_2$, —O—CF$_3$, —S(O)$_2$—R$^d$, or heteroaryl which is optionally substituted by C$_1$-C$_7$-alkyl;

R$^4$ is H, —OH, Cl, F, Br, CN, —CHF$_2$, CF$_3$, C$_1$-C$_7$-alkyl, —O—(CO)—C$_1$-C$_7$-alkyl, or —(CH$_2$)$_m$—R$^e$;

R$^5$ is C$_1$-C$_7$-alkyl, C$_1$-C$_7$-alkylC$_3$-C$_6$-cycloalkyl, —(CH$_2$)$_n$—O—R$^f$, C$_3$-C$_8$-alkenyl-O—R$^f$, —(CH$_2$)$_n$—NR$^g$R$^h$, —C$_2$-C$_6$-alkenyl-NR$^g$R$^h$, or —(CH$_2$)$_n$—R$^e$;

R$^a$ is —O—C$_1$-C$_7$-alkyl or —OH;

R$^b$ is C$_1$-C$_7$-alkyl, NH$_2$, or —O—C$_1$-C$_7$-alkyl;

R$^c$ is —OH, NH$_2$, or NH—(CO)—O—C$_1$-C$_7$-alkyl;

R$^d$ is C$_1$-C$_7$-alkyl, —NH$_2$, —NH—C$_1$-C$_7$-alkyl, or —N-di(C$_1$-C$_7$-alkyl);

R$^e$ is —OH, —CH$_2$F, —CHF$_2$, —CF$_3$, or —O—(CO)—C$_1$-C$_7$-alkyl;

R$^f$ is C$_1$-C$_7$-alkyl, C$_3$-C$_8$-alkenyl, C$_3$-C$_6$-cycloalkyl, phenyl, benzyl, or —(CO)—R';

R$^g$ and R$^h$ are each independently H, C$_1$-C$_7$-alkyl, C$_3$-C$_6$-cycloalkyl, C$_3$-C$_8$-alkenyl, phenyl, benzyl, or —(CO)—R' or R$^g$ and R$^h$, together with the nitrogen atom to which they are attached, form a 5- to 7-membered heterocyclic or heteroaryl ring optionally substituted with 1 or 2 OH;

R' is NH$_2$, —NH—C$_1$-C$_7$-alkyl, C$_1$-C$_7$-alkyl, or C$_1$-C$_7$-alkoxy;

m is 1 to 4; and n is 2 to 6;

or a pharmaceutically acceptable salt thereof.

2. The compound of claim 1:

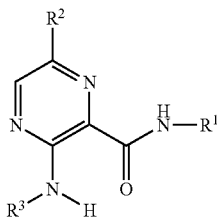 (1)

wherein

R[1] is a 5-ring selected from the group consisting of formula (IIa), (IIb), (IIc), (IId), (IIe), (IIf), and (IIg):

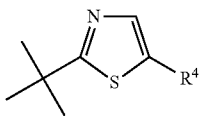 (IIa)

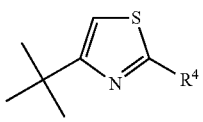 (IIb)

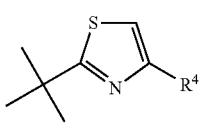 (IIc)

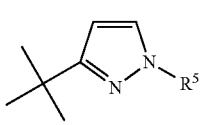 (IId)

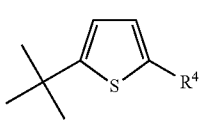 (IIe)

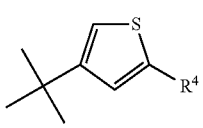 (IIf)

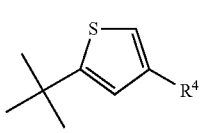 (IIg)

R[2] is H, $C_1$-$C_7$-alkyl, $C_3$-$C_6$-cycloalkyl, or —(CH$_2$)$_m$—R$^a$;
R[3] is aryl or heteroaryl each of which is optionally substituted by:
  CN, Cl, F, Br, CF$_3$, CHF$_2$, —O—$C_1$-$C_7$-alkyl, —(CO)—R$^b$, —(CH$_2$)$_m$—R$^c$, —NH—(CO)—$C_1$-$C_7$-alkyl, —O—CH$_2$F, —O—CHF$_2$, —O—CF$_3$, —S(O)$_2$—R$^d$, or heteroaryl which is optionally substituted by $C_1$-$C_7$-alkyl;
R[4] is —OH, Cl, F, Br, CN, —CHF$_2$, CF$_3$, $C_1$-$C_7$-alkyl, —O—(CO)—$C_1$-$C_7$-alkyl, or —(CH$_2$)$_m$—R$^e$;
R[5] is $C_1$-$C_7$-alkyl, $C_1$-$C_7$-alkyl-$C_3$-$C_6$-cycloalkyl, —(CH$_2$)$_n$—O—R$^f$, $C_3$-$C_8$-alkenyl-O—R$^f$, —(CH$_2$)$_n$—NR$^g$R$^h$, —$C_2$-$C_6$-alkenyl-NR$^g$R$^h$, or —(CH$_2$)$_n$—R$^e$;

R$^a$ is –O—$C_1$-$C_7$-alkyl or —OH;
R$^b$ is $C_1$-$C_7$-alkyl, NH$_2$, or —O—$C_1$-$C_7$-alkyl;
R$^c$ is —OH, NH$_2$, or NH—(CO)—O—$C_1$-$C_7$-alkyl;
R$^d$ is $C_1$-$C_7$-alkyl, —NH$_2$, —NH—$C_1$-$C_7$-alkyl, or —N-di($C_1$-$C_7$-alkyl);
R$^e$ is —OH, —CH$_2$F, —CHF$_2$, —CF$_3$, or —O—(CO)—$C_1$-$C_7$-alkyl;
R$^f$ is $C_1$-$C_7$-alkyl, $C_3$-$C_8$-alkenyl, $C_3$-$C_6$-cycloalkyl, phenyl, benzyl, or —(CO)—R';
R$^g$ and R$^h$ are each independently H, $C_1$-$C_7$-alkyl, $C_3$-$C_6$-cycloalkyl, $C_3$-$C_8$-alkenyl, phenyl, benzyl, or —(CO)—R' or R$^g$ and R$^h$, together with the nitrogen atom to which they are attached, form a 5- to 7-membered heterocyclic or heteroaryl ring optionally substituted with 1 or 2 OH;
R' is NH$_2$, —NH—$C_1$-$C_7$-alkyl, $C_1$-$C_7$-alkyl, or $C_1$-$C_7$-alkoxy;
m is 1 to 4; and
n is 2 to 6;
or a pharmaceutically acceptable salt thereof.

3. The compound of claim 1 having formula (Ia)

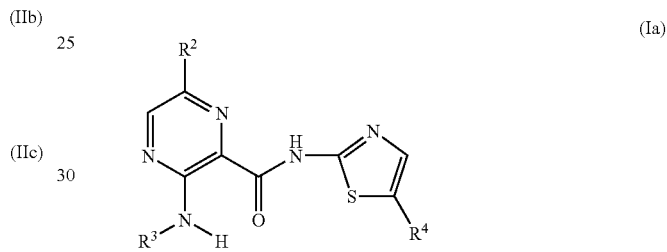 (Ia)

or a pharmaceutically acceptable salt thereof.

4. The compound of claim 3, wherein
R[2] is H or $C_1$-$C_7$-alkyl;
R[3] is phenyl or 5- or 6-membered heteroaryl each of which is optionally substituted by:
  CN, Cl, F, Br, CF$_3$, CHF$_2$, —O—$C_1$-$C_7$-alkyl, —(CO)—R$^b$, —(CH$_2$)$_m$—R$^c$, —NH—(CO)—$C_1$-$C_7$-alkyl, —O—CH$_2$F, —O—CHF$_2$, —O—CF$_3$, —S(O)$_2$—R$^d$, or heteroaryl which is optionally substituted by $C_1$-$C_7$-alkyl; and
R[4] is H, —OH, Cl, F, Br, CN, —CHF$_2$, CF$_3$, $C_1$-$C_7$-alkyl, —O—(CO)—$C_1$-$C_7$-alkyl, or —(CH$_2$)$_m$—R$^e$, or a pharmaceutically acceptable salt thereof.

5. The compound of claim 4, which is
6-Methyl-3-(pyrimidin-5-ylamino)-pyrazine-2-carboxylic acid (1-methyl-1H-pyrazol-3-yl)-amide hydrochloride.

6. The compound of claim 1 having formula (Ib)

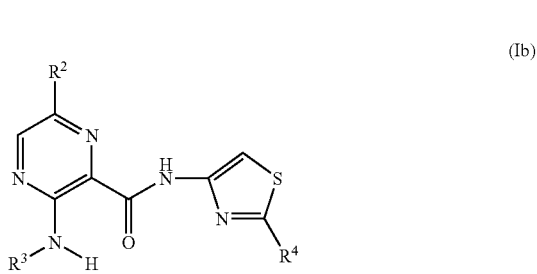 (Ib)

or a pharmaceutically acceptable salt thereof.

7. The compound of claim 6, wherein
R² is H or C₁-C₇-alkyl;
R³ is phenyl or 5- or 6-membered heteroaryl each of which is optionally substituted by:
CN, Cl, F, Br, CF₃, CHF₂, —O—C₁-C₇-alkyl, —(CO)—Rᵇ, —(CH₂)ₘ—Rᶜ, —NH—(CO)—C₁-C₇-alkyl, —O—CH₂F, —O—CHF₂, —O—CF₃, —S(O)₂—Rᵈ, or heteroaryl which is optionally substituted by C₁-C₇-alkyl; and
R⁴ is H, —OH, Cl, F, Br, CN, —CHF₂, CF₃, C₁-C₇-alkyl, —O—(CO)—C₁-C₇-alkyl, or —(CH₂)ₘ—Rᵉ, or a pharmaceutically acceptable salt thereof.

8. The compound of claim 1 having formula (Ic)

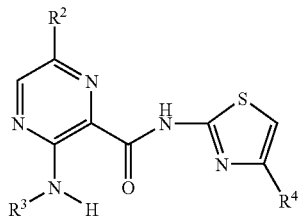

(Ic)

or a pharmaceutically acceptable salt thereof.

9. The compound of claim 8, wherein
R² is H or C₁-C₇-alkyl;
R³ is phenyl or 5- or 6-membered heteroaryl each of which is optionally substituted by:
CN, Cl, F, Br, CF₃, CHF₂, —O—C₁-C₇-alkyl, —(CO)—Rᵇ, —(CH₂)ₘ—Rᶜ, —NH—(CO)—C₁-C₇-alkyl, —O—CH₂F, —O—CHF₂, —O—CF₃, —S(O)₂—Rᵈ, or heteroaryl which is optionally substituted by C₁-C₇-alkyl; and
R⁴ is H, —OH, Cl, F, Br, CN, —CHF₂, CF₃, C₁-C₇-alkyl, —O—(CO)—C₁-C₇-alkyl, or —(CH₂)ₘ—Rᵉ, or a pharmaceutically acceptable salt thereof.

10. The compound of claim 1 having formula (Id)

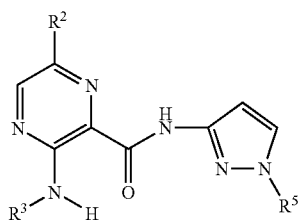

(Id)

or a pharmaceutically acceptable salt thereof.

11. The compound of claim 10, wherein:
R² is H or C₁-C₇-alkyl;
R³ is H, phenyl or 5- or 6-membered heteroaryl each of which is optionally substituted by:
CN, Cl, F, Br, CF₃, CHF₂, —O—C₁-C₇-alkyl, —(CO)—Rᵇ, —(CH₂)ₘ—Rᶜ, —NH—(CO)—C₁-C₇-alkyl, —O—CH₂F, —O—CHF₂, —O—CF₃, —S(O)₂—Rᵈ, or heteroaryl which is optionally substituted by C₁-C₇-alkyl; and
R⁵ is C₁-C₇-alkyl, C₁-C₇-alkyl-C₃-C₆-cycloalkyl, —(CH₂)ₙ—O—Rᶠ, C₃-C₈-alkenyl-O—Rᶠ, —(CH₂)ₙ—NRᵍRʰ, —C₂-C₆-alkenyl-NRᵍRʰ, or —(CH₂)ₙ—Rᵉ, or a pharmaceutically acceptable salt thereof.

12. The compound of claim 1 having formula (Ie)

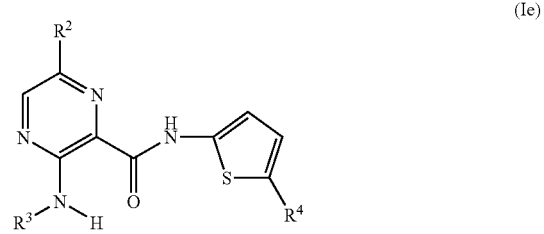

(Ie)

or a pharmaceutically acceptable salt thereof.

13. The compound of claim 1 having formula (If)

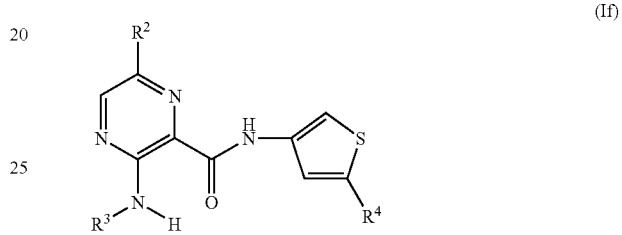

(If)

or a pharmaceutically acceptable salt thereof.

14. The compound of claim 1 having formula (Ig)

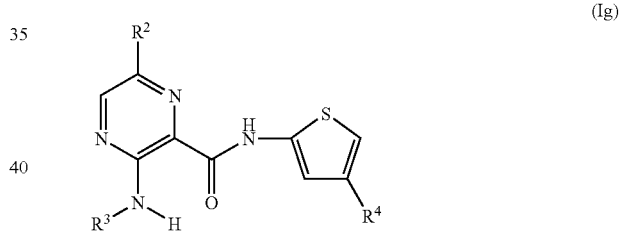

(Ig)

or a pharmaceutically acceptable salt thereof.

15. The compound of claim 1, wherein
R³ is aryl which is optionally substituted by CN, Cl, F, Br, CHF₂, —O—C₁-C₇-alkyl, —(CO)—Rᵇ, —(CH₂)ₙ—Rᶜ, —NH—(CO)—C₁-C₇-alkyl, —O—CH₂F, —O—CHF₂, —O—CF₃, S(O)₂—Rᵈ, or heteroaryl which is optionally substituted by C₁-C₇-alkyl.

16. The compound of claim 1, wherein
R³ is heteroaryl which is optionally substituted by CN, Cl, F, Br, CHF₂, —(CO)—Rᵇ, —(CH₂)ₙ—Rᶜ, —NH—(CO)—C₁-C₇-alkyl, —O—CH₂F, —O—CHF₂, —O—CF₃, S(O)₂—Rᵈ, or heteroaryl which is optionally substituted by C₁-C₇-alkyl.

17. The compound of claim 7, which is 6-Methyl-3-(pyrimidin-5-ylamino)-pyrazine-2-carboxylic acid (2-methyl-thiazol-4-yl)-amide hydrochloride.

18. The compound of claim 9, selected from the group consisting of
3-(3-Fluoro-phenylamino)-pyrazine-2-carboxylic acid (4-methyl-thiazol-2-yl)-amide

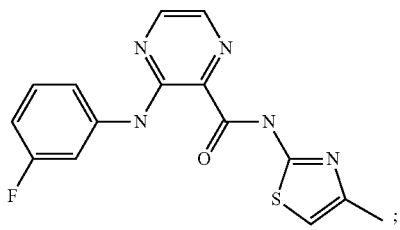

3-(Pyridin-3-ylamino)-pyrazine-2-carboxylic acid (4-methyl-thiazol-2-yl)amide dihydrochloride

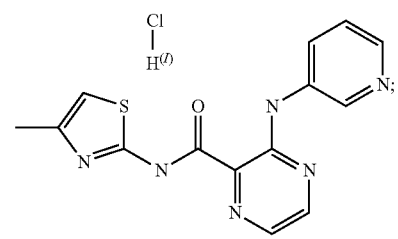

3-(Pyrimidin-5-ylamino)-pyrazine-2-carboxylic acid (4-methyl-thiazol-2-yl)-amide

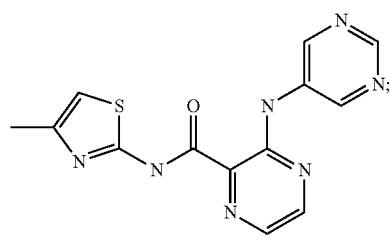

6-Methyl-3-(pyridin-3-ylamino)-pyrazine-2-carboxylic acid (4-methyl-thiazol-2-yl)-amide hydrochloride

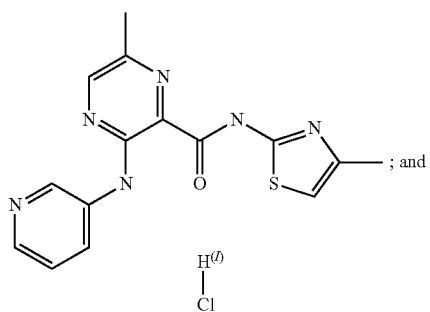

6-Methyl-3-(pyrimidin-5-ylamino)-pyrazine-2-carboxylic acid (4-methyl-thiazol-2-yl)-amide

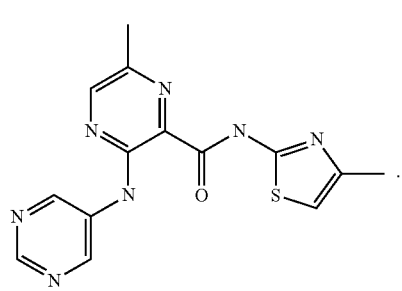

19. The compound of claim 11, selected from the group consisting of 3-(5-Fluoro-pyridin-3-ylamino)-pyrazine-2-carboxylic acid (1-methyl-1H-pyrazol-3-yl)-amide

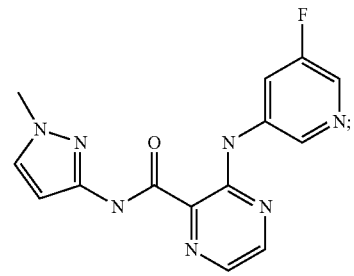

6-Methyl-3-(pyridin-3-ylamino)-pyrazine-2-carboxylic acid (1-methyl-1H-pyrazol-3-yl)-amide hydrochloride

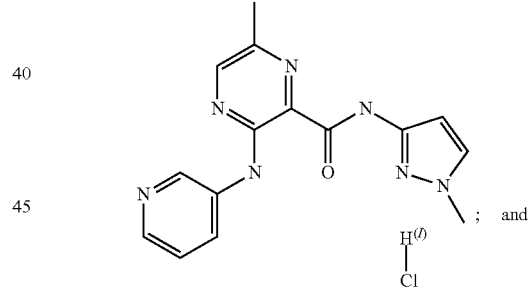

6-Methyl-3-(pyrimidin-5-ylamino)-pyrazine-2-carboxylic acid (1-methyl-1H-pyrazol-3-yl)-amide hydrochloride

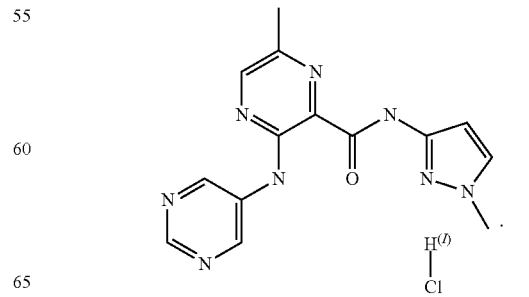

20. The compound of claim 12, wherein:
$R^2$ is H or $C_1$-$C_7$-alkyl;
$R^3$ is phenyl or 5- or 6-membered heteroaryl each of which is optionally substituted by:
CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl; and
$R^4$ is H, —OH, Cl, F, Br, CN, —$CHF_2$, $CF_3$, $C_1$-$C_7$-alkyl, —O—(CO)—$C_1$-$C_7$-alkyl, or —$(CH_2)_m$—$R^e$, or a pharmaceutically acceptable salt thereof.

21. The compound of claim 13, wherein
$R^2$ is H or $C_1$-$C_7$-alkyl;
$R^3$ is phenyl or 5- or 6-membered heteroaryl each of which is optionally substituted by:
CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl; and
$R^4$ is H, —OH, Cl, F, Br, CN, —$CHF_2$, $CF_3$, $C_1$-$C_7$-alkyl, —O—(CO)—$C_1$-$C_7$-alkyl, or —$(CH_2)_m$—$R^e$, or a pharmaceutically acceptable salt thereof.

22. The compound of claim 14, wherein
$R^2$ is H or $C_1$-$C_7$-alkyl;
$R^3$ is phenyl or 5- or 6-membered heteroaryl each of which is optionally substituted by CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl; and
$R^4$ is H, —OH, Cl, F, Br, CN, —$CHF_2$, $CF_3$, $C_1$-$C_7$-alkyl, —O—(CO)—$C_1$-$C_7$-alkyl, or —$(CH_2)_m$—$R^e$, or a pharmaceutically acceptable salt thereof.

23. A pharmaceutical composition comprising a therapeutically effective amount of a compound of formula (I)

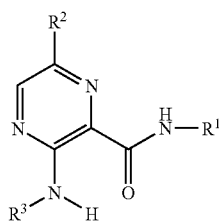

(I)

wherein
$R^1$ is a 5-ring selected from the group consisting of formula (IIa), (IIb), (IIc), (IId), (IIe), (IIf), and (IIg):

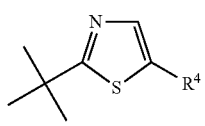

(IIa)

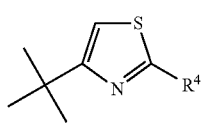

(IIb)

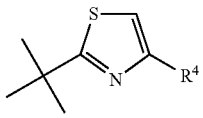

(IIc)

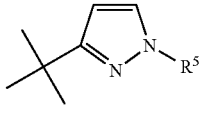

(IId)

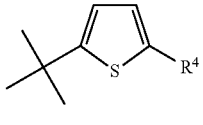

(IIe)

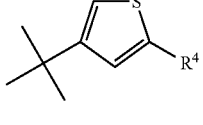

(IIf)

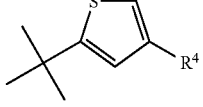

(IIg)

$R^2$ is H, $C_1$-$C_7$-alkyl, $C_3$-$C_6$-cycloalkyl, or —$(CH_2)_m$—$R^a$;
$R^3$ is aryl, or heteroaryl each of which is optionally substituted by:
CN, Cl, F, Br, $CF_3$, $CHF_2$, —O—$C_1$-$C_7$-alkyl, —(CO)—$R^b$, —$(CH_2)_m$—$R^c$, —NH—(CO)—$C_1$-$C_7$-alkyl, —O—$CH_2F$, —O—$CHF_2$, —O—$CF_3$, —$S(O)_2$—$R^d$, or heteroaryl which is optionally substituted by $C_1$-$C_7$-alkyl;
$R^4$ is H, —OH, Cl, F, Br, CN, —$CHF_2$, $CF_3$, $C_1$-$C_7$-alkyl, —O—(CO)—$C_1$-$C_7$-alkyl, or —$(CH_2)_m$—$R^e$;
$R^5$ is $C_1$-$C_7$-alkyl, $C_1$-$C_7$-alkyl-$C_3$-$C_6$-cycloalkyl, —$(CH_2)_n$—O—$R^f$, $C_3$-$C_8$-alkenyl-O—$R^f$, —$(CH_2)_n$—$NR^gR^h$, —$C_2$-$C_6$-alkenyl-$NR^gR^h$, or —$(CH_2)_n$—$R^e$;
$R^a$ is —O—$C_1$-$C_7$-alkyl or —OH;
$R^b$ is $C_1$-$C_7$-alkyl, $NH_2$, or —O—$C_1$-$C_7$-alkyl;
$R^c$ is —OH, $NH_2$, or NH—(CO)—O—$C_1$-$C_7$-alkyl;
$R^d$ is $C_1$-$C_7$-alkyl, —$NH_2$, —NH—$C_1$-$C_7$-alkyl, or —N-di($C_1$-$C_7$-alkyl);
$R^e$ is —OH, —$CH_2F$, —$CHF_2$, —$CF_3$, or —O—(CO)—$C_1$-$C_7$-alkyl;
$R^f$ is $C_1$-$C_7$-alkyl, $C_3$-$C_8$-alkenyl, $C_3$-$C_6$-cycloalkyl, phenyl, benzyl, or —(CO)—R';
$R^g$ and $R^h$ are each independently H, $C_1$-$C_7$-alkyl, $C_3$-$C_6$-cycloalkyl, $C_3$-$C_8$-alkenyl, phenyl, benzyl, or —(CO)—R' or $R^g$ and $R^h$, together with the nitrogen atom to which they are attached, form a 5- to 7-membered heterocyclic or heteroaryl ring optionally substituted with 1 or 2 OH;
R' is $NH_2$, —NH—$C_1$-$C_7$-alkyl, $C_1$-$C_7$-alkyl, or $C_1$-$C_7$-alkoxy;
m is 1 to 4; and
n is 2 to 6;
or a pharmaceutically acceptable salt thereof and a pharmaceutically acceptable carrier.

* * * * *